(12) United States Patent
Katsumata et al.

(10) Patent No.: US 9,084,568 B2
(45) Date of Patent: Jul. 21, 2015

(54) RADIATION IMAGING APPARATUS AND IMAGING METHOD USING RADIATION

(75) Inventors: Akitoshi Katsumata, Ichinomiya (JP); Koichi Ogawa, Nakano-ku (JP); Tsutomu Yamakawa, Nishinomiya (JP); Masahiro Tsujita, Ikoma (JP); Tatsuya Nagano, Takatsuki (JP); Kazuhide Kitou, Mino (JP)

(73) Assignee: Telesystems Co., Ltd., Osaka (JP)

( * ) Notice: Subject to any disclaimer, the term of this patent is extended or adjusted under 35 U.S.C. 154(b) by 542 days.

(21) Appl. No.: 13/387,827

(22) PCT Filed: Aug. 5, 2010

(86) PCT No.: PCT/JP2010/063266
§ 371 (c)(1),
(2), (4) Date: Sep. 13, 2012

(87) PCT Pub. No.: WO2011/016508
PCT Pub. Date: Feb. 10, 2011

(65) Prior Publication Data
US 2012/0328071 A1    Dec. 27, 2012

(30) Foreign Application Priority Data

Aug. 5, 2009    (JP) ................................. 2009-182310

(51) Int. Cl.
| | | |
|---|---|---|
| *A61B 6/14* | (2006.01) | |
| *A61B 6/00* | (2006.01) | |
| *A61B 6/03* | (2006.01) | |

(52) U.S. Cl.
CPC . *A61B 6/14* (2013.01); *A61B 6/037* (2013.01); *A61B 6/4028* (2013.01); *A61B 6/469* (2013.01); *A61B 6/5223* (2013.01)

(58) Field of Classification Search
CPC ... G06T 11/003; G06T 11/005; G06T 11/006; H04N 5/23238; A61B 6/032; A61B 6/037; A61B 6/14; A61B 6/4028; A61B 6/4233; A61B 6/4441; A61B 6/469; A61B 6/547

USPC ............ 378/4, 11, 13, 15, 38, 39, 40, 41, 51, 378/55, 62, 64, 176, 193, 205
See application file for complete search history.

(56) References Cited

U.S. PATENT DOCUMENTS

| | | | | |
|---|---|---|---|---|
| 6,196,715 | B1 | 3/2001 | Nambu et al. | |
| 7,039,239 | B2 * | 5/2006 | Loui et al. | ...................... 382/225 |

(Continued)

FOREIGN PATENT DOCUMENTS

| | | | | |
|---|---|---|---|---|
| EP | 1961383 | * | 4/2007 | ............... A61B 6/14 |
| JP | 57-203430 | A | 12/1982 | |

(Continued)

OTHER PUBLICATIONS

Nikaido et al, a phase-based image registration algorithm for dental radiograph identification, Sep.-Oct. 2007, IEEE ICIP, vol. 6, p. 229, 230.*

(Continued)

*Primary Examiner* — Glen Kao
*Assistant Examiner* — Julio M Duarte-Carvajali
(74) *Attorney, Agent, or Firm* — Harness, Dickey & Pierce, PLC

(57) ABSTRACT

A radiation imaging apparatus is provided. The apparatus has moving means moving a pair of an X-ray tube and a detector relatively to an object. The apparatus further has means which acquire digital frame data outputted from the detector. The frame data are acquired from the same portion being imaged of the same object at different time points. The apparatus has means which use the frame data to produce a plurality of three-dimensional optimally focused images at the respective time points, an actual position and shape of the portion being imaged being reflected in the images, and means which estimate changes of the plural three-dimensional optimally focused images.

5 Claims, 29 Drawing Sheets

(56) References Cited

U.S. PATENT DOCUMENTS

| | | |
|---|---|---|
| 7,336,763 B2 | 2/2008 | Spartiotis et al. |
| 7,778,388 B2 | 8/2010 | Sendai |
| 2005/0113961 A1* | 5/2005 | Sabol et al. .................. 700/182 |

FOREIGN PATENT DOCUMENTS

| | | |
|---|---|---|
| JP | 4-144548 A | 5/1992 |
| JP | 06-088790 A | 3/1994 |
| JP | 2007-136163 A | 6/2007 |
| JP | 2010-148676 A | 7/2010 |

OTHER PUBLICATIONS

Koichi Ito, et al., "A Palmprint Recognition Algorithm Using Phase-Only Correlation", Meeting on Image Recognition & Understanding (MIRU 2006); Issued Jul. 2006; pp. 370-375 (with English Abstract).

* cited by examiner

FIG.15(1)
(A) 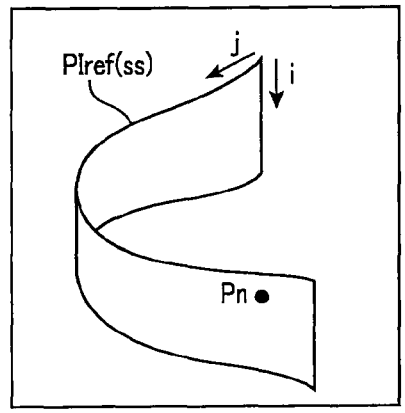
(B) 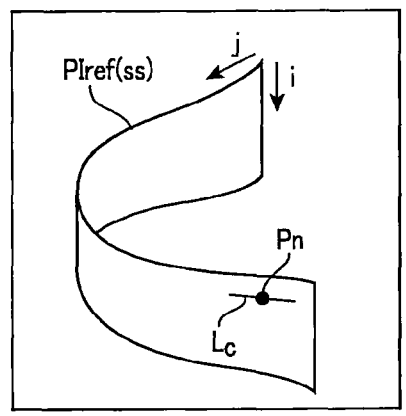
(C) 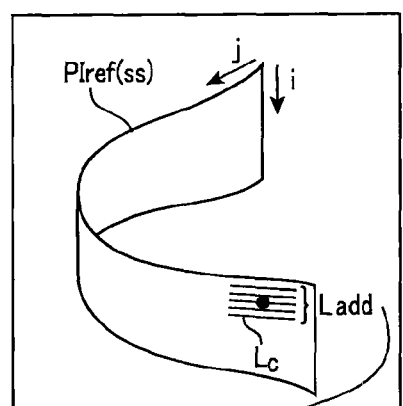
(D) 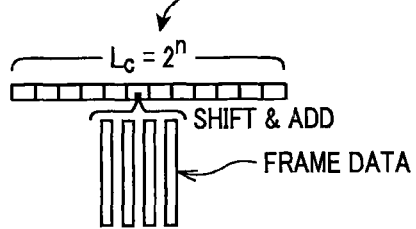

RADIATION IMAGING APPARATUS AND IMAGING METHOD USING RADIATION

FIELD OF THE INVENTION

The present invention relates to a radiation imaging apparatus and an imaging method using the radiation which acquire images of an object being imaged based on a tomosynthesis technique, and in particular, to a radiation imaging apparatus and an imaging method using the radiation, which are able to estimate temporal changes of an imaged part from a plurality of images provided by imaging the same part of the same object at different times.

BACKGROUND ART

In recent years, tomographic imaging using a tomosynthesis technique has been used actively. The theory of this tomosynthesis technique has been known long before (for example, refer to patent literature 1), and recently, tomographic imaging that enjoys ease of image reconstruction performed using the tomosynthesis technique has been proposed (for example, refer to patent literatures 2 and 3). Especially, many such cases can be found in dental and mammographic fields (for example, refer to patent literatures 4, 5 and 6).

In the dental field, tomosynthesis technique is usually put into practical use as a panoramic imaging apparatus that acquires panoramic images in which a curved tooth row is usually expanded into a two-dimensional plane. This panoramic imaging apparatus is usually provided with a mechanism that rotates a pair of an X-ray tube and an X-ray detector around the oral cavity of an object being imaged. The X-ray detector has pixels mapped in a rectangle with a portrait-oriented width. The mechanism rotates the pair of the X-ray tube and the X-ray detector with a rotation center thereof intricately so that the rotation center traces a predetermined orbit which is previously set along a tooth row. The predetermined orbit is set to focus on a 3D referential tomographic plane previously set along a tooth row which can be regarded as a tooth row having a standard shape and size. During the rotation, an X-ray beam is radiated from the X-ray tube at given intervals and the X-ray (i.e., X-ray beams or X-rays) is transmitted through the object to be received by the X-ray detector, and digital frame data is detected from the detector. In this way, the frame data focusing on the 3D referential tomographic plane is acquired at the given intervals. These frame data are subjected to reconstruction using the tomosynthesis technique so as to provide a panoramic image of the 3D referential tomographic plane.

However, the foregoing conventional panoramic imaging apparatuses do not take it account the fact that there are differences between the tooth row of each object and the 3D referential tomographic plane and positioning tooth rows involves difficult operations. As might be expected, there are individual differences in the shapes and sizes of the tooth rows of respective objects. The sizes of objects' jaws differ depending on the individuals, making it difficult to correctly position the tooth rows. This often causes defocused panoramic images to be reconstructed, which may fail to meet a demand for fine interpretation of the images. In such cases, if it is desired to finely examine cases including cavities and alveolar pyorrhea, it is needed to perform intraoral imaging or dental CT imaging, separately from the panoramic imaging. Re-performance of the panoramic imaging and X-ray imaging using another modality will raise the amount of X-rays to which the object is exposed.

In order to try to overcome such difficulties, there is provided an apparatus provided by patent reference 7. In the panoramic imaging apparatus shown in this publication, a phantom is used to previously measure gains (i.e., distance information for mutual addition of frame data) and positions in each of depth directions of a tooth row. Additionally, acquired frame data are used to produce a focus-optimized image of the 3D referential tomographic plane using the tomosynthesis technique. In the focus-optimized image, a ROI is set to specify a partial region of the tooth row, and a focus-optimized image at a selected position in the front-back direction (i.e., each of front-back directions of the tooth row, which connect the X-ray tube and the X-ray detector at each of the radiation positions) of the partial region are reconstructed using already acquired frame data and a gain necessary among the gains which have been measured. Hence, the data acquisition is performed one time with the 3D referential tomographic plane focused, and then, a focus-optimized image of any partial region can be reconstructed by making use of the already acquired frame data.

PRIOR ART REFERENCE

Patent Reference

[Patent Reference 1] JP-A-S57-203430
[Patent Reference 2] JP-A-H6-88790
[Patent Reference 3] JP-A-H10-295680
[Patent Reference 4] JP-A-H4-144548
[Patent Reference 5] JP-A-2008-110098
[Patent Reference 6] US2006/0203959 A1
[Patent Reference 7] JP-A-2007-136162

SUMMARY OF THE INVENTION

Issues to be Solved by the Invention

However, the panoramic imaging apparatus provided by the patent reference 7 does not consider the fact that teeth being imaged are curved or warped in their longitudinal directions. It is usual that each tooth of a tooth row is not at the same longitudinal position. It is frequent that the teeth are curved inwards in the oral cavity as advancing to the base thereof. It is thus difficult to focus on all the areas of each tooth on one section. With consideration of this regard, it is necessary to focus on all the longitudinal areas of the teeth to raise depiction performance thereof. In other words, though the foregoing panoramic imaging apparatus can focus on any partial region located at an arbitrary position in the front-back direction, it is difficult to obtain one panoramic image which is focused through the entire areas of a tooth row. Even when best-focused partial images are connected to represent an entire panoramic image, there are caused irregularities between connected edges of the partial images, thus spoiling the connection.

The foregoing difficulties are aggravated by the fact that enlargement factors in the longitudinal and lateral directions of an image (i.e., the longitudinal and width directions of the tooth row) differ depending on changes in the rotation center position of the pair of the X-ray tube and the detector during the scanning. The enlargement factor is defined as a ratio between the actual size of a tooth and the size of an enlarged image of the tooth, of which shadow is projected to the X-ray incident surface of the X-ray detector. Since the X-ray tube has an X-ray source which is small enough which can be regarded as a point source, the X-rays are radiated from the point X-ray source. However, in reconstructing a tooth row in a 3D tomographic plane based on the tomosynthesis technique, the lateral enlargement of a reconstructed image is the same at any positions on the image, but the longitudinal scaling thereof differs at the various positions. This causes a reconstructed panoramic image to be distorted more than an actual tooth row in the lateral direction. In addition, the scaling, that is, the degree of the distortion differs depending on where a tooth is located, i.e. in the anterior teeth or both side molar teeth (i.e., teeth on the back side), affects the longitudinal shapes thereof, thus causing distortion among the teeth in a panoramic image. Still, when a tooth row is not entirely or partially along a given 3D referential tomographic plane, the distortion of portions of the tooth row, which is due to differences of the scaling in both the longitudinal and lateral directions, will be increased more severely.

In the conventional panoramic imaging apparatus in which digital-quantity frame data are acquired to reconstruct a panoramic image thereon, post processing is often carried out to remedy the foregoing difficulty. In this post processing, a reconstructed image is multiplied by coefficients which allow the sizes of the teeth to be shortened such that the ratio between the longitudinal and lateral enlargements becomes the same, at least, at the center of the anterior teeth area. Even in such a remedy, the height of the molar teeth is depicted smaller than the actual size thereof in the panoramic image. That is, there remains distortion among the individual teeth due to the fact that the enlargement factor differs positionally.

In this way, the difficulty resulting from differences of the enlargement factor has not been overcome, and optimally focusing on the entire region of an object in a panoramic image has not been realized. It is thus frequently difficult to interpret and diagnose teeth and/or the gum depicted in the conventional panoramic image. Particularly it is difficult to reliably measure lengths and distances in such images. Hence, for instance, implant placement is confronted with a difficulty of positioning implanted portions with the required accuracy.

As a conventional countermeasure to compensate such difficulties as much as possible, a marker to indicate a reference position is attached to a desired position in the oral cavity before imaging, so that the reference position is given in an image. With reference to the reference position, the image is corrected to maintain accuracy, so that the foregoing difficulty is compensated as much as possible. However, in this measure, steps for imaging and diagnosis become complex. An operational burden on operators is heavier. Thus, due to such reasons, the marker cannot be used easily for preventive practice such a screening test. It is therefore highly needed to provide panoramic images which can be used widely from the preventive measure such as screening to complicated treatment such as implant placement.

In addition, a three-dimensional panoramic image would be useful for diagnosing the whole structure of a tooth row in its back-and-forth direction. However, images which meet such a need and overcome the freeing various difficulties have not been provided yet.

Moreover, in the condition with which the above conventional techniques are faced, it is hardly possible to interpret temporal changes of the same tooth row of the same patient using the conventional panoramic images. To observe such temporal changes, it is necessary to perform imaging a plurality of times with time therebetween. For instance, in such situations as observing changes of cavities and performing an implant treatment, it is required to image teeth before and after the treatment. In general the oral cavity of the same patient is slightly shifted in its spatial position, though the oral cavity is positioned for each imaging. This shift depends on various factors including shifts of positioning carried out by an operator. Hence, it is almost impossible to image such temporal changes using conventional panoramic images.

In consideration of the foregoing, it is an object of the present invention to provide a radiation imaging technique which is able to obtain a three-dimensional optimally focused image where image distortion due to differences of the enlargement factor is almost removed to depict, with a higher degree of accuracy, the actual position and shape of an portion being imaged of an object, and provide information indicative of temporal changes in the same part being imaged of the same object using the obtained the three-dimensional optimally focused image.

Means for Solving the Issues

In order to achieve the object, the present invention provides a radiation imaging apparatus, a data processing apparatus, an imaging method using the radiation, and a computer program.

Of these, the radiation imaging apparatus has, as its essence, a radiation emitting source that emits radiation; a radiation detector that outputs, every frame, electric digital two-dimensional data corresponding to incidence of the radiation to the radiation detector; moving means for moving a pair of the radiation emitting source and the radiation detector, the radiation detector, or an object being imaged relatively to a remaining one among the radiation emitting source, the radiation detector, and the object; data acquiring means for acquiring, every frame, the data outputted from the radiation detector while the pair of the radiation emitting source and the radiation detector, the radiation detector, or the object is moved relatively to the remaining one by the moving means; image producing means for producing a plurality of three-dimensional optimally focused images on the basis of the data acquired by the data acquiring means at different time points from the same portion to be imaged of the object, the portion to be imaged of the object being optimally focused and reflecting an actual position and shape of the portion therein; and estimating means for estimating an amount of changes among the plurality of three-dimensional optimally focused images produced by the image producing means at the different time points.

In addition, a data processing apparatus processes data outputted from a system having a radiation emitting source, a radiation detector, moving means, and data acquiring means, which are identical to the foregoing. The data processing apparatus also has the foregoing image producing means and estimating means.

Furthermore, the imaging method using radiation includes, as its essence, a data acquiring step of acquiring data, frame by frame, outputted from a radiation detector during movement of a pair of a radiation emitting source and the radiation detector, the radiation detector, or an object being imaged relatively to a remaining one among the radiation emitting source, the radiation detector, and the object, wherein the radiation detector that outputs, every frame, electric digital two-dimensional data serving as the data and corresponding to incidence of the radiation to the radiation detector; an image producing step of producing a plurality of three-dimensional optimally focused images on the basis of the data acquired in the data acquiring step at different time points from the same portion to be imaged of the object, the portion to be imaged of the object being optimally focused and reflecting an actual size and shape of the portion thereon; and an estimating step of estimating amounts of changes among the plurality of three-dimensional optimally focused images produced in the image producing step at the different time points.

Furthermore, there is provided a program for computers, wherein the program is previously stored in a memory and readable from the memory and which allows a computer to process data from a system comprising: a radiation emitting source that emits radiation; a radiation detector that outputs, every frame, electric digital two-dimensional data serving as the data from system and corresponding to incidence of the radiation to the radiation detector; moving means for moving a pair of the radiation emitting source and the radiation detector, the radiation detector, or an object being imaged relatively to a remaining one among the radiation emitting source, the radiation detector, and the object; and data acquiring means for acquiring, every frame, the data outputted from the radiation detector while the pair of the radiation emitting source and the radiation detector, the radiation detector, or the object is moved relatively to the remaining one by the moving means. The program allows the computer to functionally perform an image producing step of producing a plurality of three-dimensional optimally focused images on the basis of the data acquired by the data acquiring means at different time points from the same portion to be imaged of the object, the portion to be imaged of the object being optimally focused and reflecting an actual size and shape of the portion thereon; and an estimating step of estimating an amount of changes among the plurality of three-dimensional optimally focused images produced in the image producing step at the different time points.

Effects of the Invention

By using a radiation imaging apparatus, a data processing apparatus, an imaging method using radiation, and a program for computers according to the present invention, there can be provided three-dimensional optimally focused images. From the images, most distortion due to differences among enlargement factors is removed. The actual position and shape of a portion being imaged of an object are reflected with a high degree of accuracy in the images. Using the three-dimensional optimally focused images, information indicative of temporal and spatial changes of the same portion being imaged of the same object, can be produced In other words, three-dimensional optimally focused images obtained by imaging the same portion of the same object at different timings can be used to reliably estimate information showing such changes. The estimation includes depiction of temporal changes of the portion being imaged and depiction of amounts of changes.

BRIEF DESCRIPTION OF THE DRAWINGS

FIG. 15(2) is a view explaining, together with FIG. 15(1), the process to identify optimally-focused tomographic planes for each of positions on the 3D reference image;

DETAILED DESCRIPTION OF PREFERRED EMBODIMENTS

With reference to the accompanying drawings, embodiments of the present invention will now be described.

Embodiment

Referring to FIGS. 1-31, an embodiment of a radiation imaging apparatus and a method of imaging using a radiation, which are according to the present invention, will now be described. These apparatus and method are put into practice as a dental panoramic imaging apparatus that uses X-rays (X-ray beams). This panoramic imaging apparatus will now be described.

Figure 1:
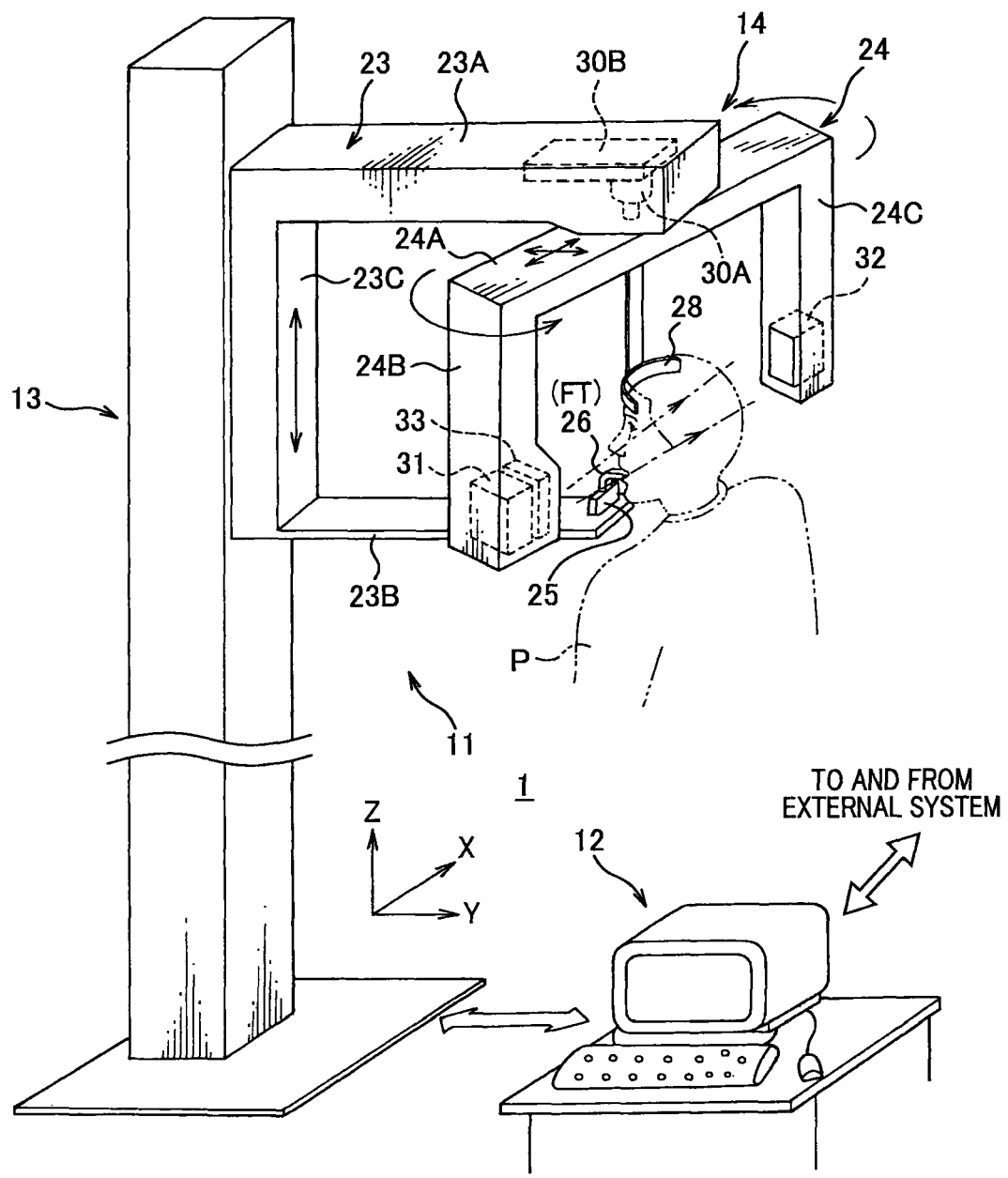
FIG. 1 is a perspective view outlining the whole configuration of an X-ray panoramic imaging apparatus employed as a radiation imaging apparatus according to one embodiment of the present invention.

FIG. 1 outlines the appearance of the panoramic imaging apparatus 1. This panoramic imaging apparatus 1 is able to scan, with an X-ray beam, the jaw of an object to obtain digital X-ray transmission data, and use the data to provide a 3D (three-dimensional) image (i.e., later-described 3D autofocus image) in which the actual position and shape (generically referred to as a real position) of the tooth row of a three-dimensional structure is identified. In particular this panoramic imaging apparatus 1 has a basic performance that provides information indicating temporal changes between or among a plurality of (e.g., two) 3D autofocus images obtained at different imaging times which differ from each other in the temporal sequence (for example, two imaging times with two weeks left therebetween). Incidentally the present embodiment uses a tomosynthesis technique in obtaining 3D autofocus images and uses a Phase-only correlation technique in the process of obtaining information indicating the temporal changes.

The configuration of this panoramic imaging apparatus 1 will now be outlined. As shown in FIG. 1, this apparatus 1 is provided with a gantry 11 with which data is acquired from an object (patient) P who is in a standing position, for example, and a control & calculation apparatus 12 realized by use of a computer. The control & calculation apparatus 12 is configured to control data acquisition performed by the frame 11, produce panoramic images based on the acquired data, and post-process the panoramic images in an interactive or manual manner with an operator (doctor or medical operator).

The frame 11 has a standing unit 13 and an imaging unit 14 movable upward and downward relative to the standing unit 13. The imaging unit 14 is attached to the pillar of the standing unit 13 to be movable upward and downward in a predetermined range.

For the sake of easier explanation, the panoramic imaging apparatus is given the XYZ orthogonal coordinate system whose Z-axis is assigned to the longitudinal direction, i.e., the vertical direction, of the standing unit 13. Incidentally, a two-dimensional panoramic image, described later, is represented with its abscissa axis defined as a j-axis and its ordinate axis defined as an i-axis (i.e, Z-axis).

The imaging unit 14 includes a vertical movement unit 23 whose side appearance is approximately C-shaped and a rotation unit 24 rotatably (turnably) supported by the vertical movement unit 23. The vertical movement unit 23 is movable in a given range of height in the Z-axis direction (longitudinal direction) by a not-shown vertical movement mechanism (for example, a motor and a lack/pinion device) arranged in the standing unit 13. A command for this movement is provided from the control/I/calculation apparatus 12 to the vertical movement mechanism.

As described, the vertical movement unit 23 has a side appearance which is approximately C-shaped, and an upper arm 23A and a lower arm 23B located on the upper and lower sides respectively and a longitudinal arm 23C integrally connecting the upper and lower arms 23A and 23B. The longitudinal arm 23C is movably, in the vertical direction, supported on the foregoing standing unit 13. Of these arms 23A-23C, the upper arm 23A and the longitudinal arm 23C cooperatively provide an imaging space (real space). Inside the upper arm 23A, a rotary drive mechanism 30A for rotary drive (for example, an electric motor and a reduction gear) is arranged. The rotary drive mechanism 30A receives a command for rotary drive from the control/I/calculation apparatus 12. This mechanism 30A has an output shaft, which is the rotation shaft of the electric motor, arranged to protrude from the upper arm 23A downward (downward in the Z-axis direction). To this rotation shaft, the rotation unit 24 is rotatably coupled. That is, the rotation unit 24 is arranged downward from the vertical movement unit 23, and rotates responsively to the drive of the rotary drive mechanism 30A.

The rotary drive mechanism 30A is linked with a movement mechanism 30B. This movement mechanism 30B is composed of devices such as a not-shown electric motor and gears. This mechanism 30B is also driven responsively to a command for rotary drive from the control & calculation apparatus 12, and is capable of moving the rotary drive mechanism 30A, i.e., the rotation unit 24 along the X-Y plane. Hence, the rotation center of a pair of an X-ray tube and a detector, which will be described later, can be moved to two-dimensionally trace a later-described trajectory which is along a given orbit in a predetermined range of the X-Y plane.

Meanwhile, the lower arm 22B extends to have a predetermined length in the same direction as that of the upper arm 23A. A chin rest 25 is placed on a tip end of the lower arm. A bite block 26 (or simply bite) is detachably attached to the chin rest 25. An object P, i.e., patient, bites the bite block 26, so that the chin rest 25 and the bite block 26 provide a function of positioning the oral cavity of the objet P.

The rotation unit 24 has also an approximately C-shaped appearance when being viewed from one side thereof in its used state, where the rotation unit is rotatably attached to the motor output shaft of the upper arm 23A, with its opened end side directed downward. Practically, the rotation unit has a lateral arm 24A rotatable (turnable) parallel with the lateral direction, that is, the X-Y plane and right and left vertical arms (the first and second vertical arms) extending downward (in the Z-axis direction) from both ends of the lateral arm 24A. The lateral arm 24A and the first and second arms 24B and 24C, which are the right and left arms, are located within the imaging space (the real space), and driven to operate under the control of the control & calculation apparatus 12.

At an inner lower end of the first vertical arm 24B, an X-ray tube 31 is provided which functions as a radiation emitting source. This X-ray tube 31 is for example a rotating anode X-ray tube and has a target (anode) which radially emits X-rays toward the second vertical arm 24C. The focus of an electron beam made to collide with the target is as small in radius as 0.5-1 mm, that is, the X-ray tube 31 has a point X-ray source. On the X-ray output side of the X-ray tube 31, there is provided a collimator 33 having a slit. This slit collimates a comparatively thin beam-shaped X-ray, which is incident to the detector 32, to an actual acquiring window (for example, a window whose width is 5.0 mm) of the detector. Elements that compose the radiation emitting source may include this collimator 33.

In contrast, at an inner lower end of the second vertical arm 24C, there is provided, as a radiation detecting means, a digital type of X-ray detector 32 equipped with X-ray detection elements two-dimensionally arrayed (for example, arrayed in a matrix of 64×1500) and produced to detect the incident X-rays through the incidence window. By way of example, this detector 32 has a longitudinally-long shaped detecting portion (for example, 6.4 mm width×150 mm long) which is made of CdTe. In the present embodiment, since the tomosynthesis technique is adopted, it is indispensable to provide the detector 32 with a plurality of X-ray detecting elements in its lateral (width) direction.

The detector 32 is arranged such that its longitudinal direction agrees with the Z-axis direction. The detector 32 has a lateral effective width which is set to, for example, approximately 5.0 mm by the foregoing collimator 33. This detector 32 is capable of acquiring digital image data in accordance with amounts of incident X-rays at a frame rate of, for example, 300 fps (for example, 64×1500 pixels per frame). The acquired data are called "frame data."

Figure 2:
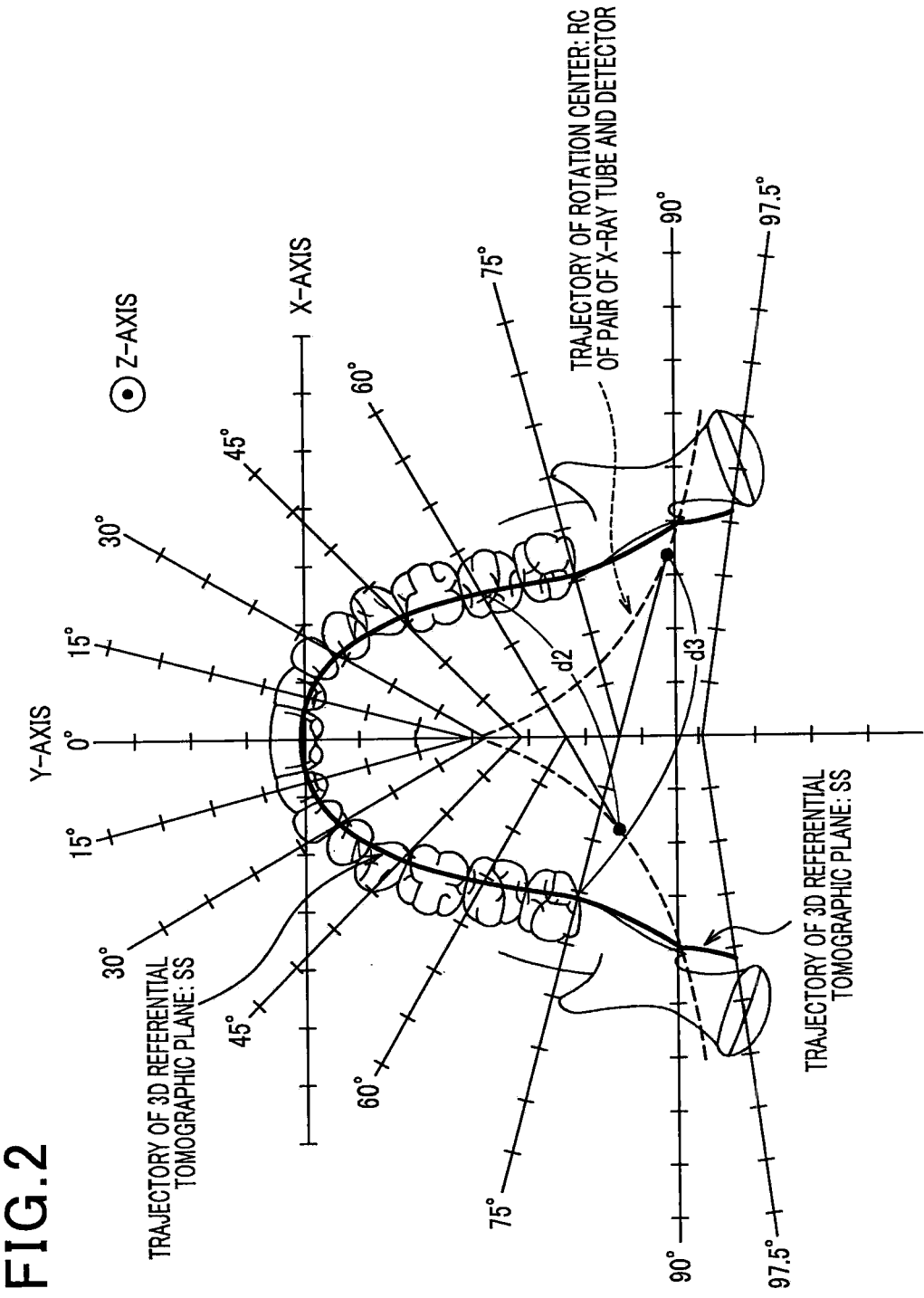
FIG. 2 is a view explaining the tooth row of an object being examined by the panoramic imaging apparatus according to the embodiment, a 3D referential tomographic plane which is set at the tooth row, and a trajectory of a rotation center on which a pair of an X-ray tube and a detector rotates.

During imaging, the X-ray tube 31 and the detector 32 are located to be opposed to each other with the oral cavity of the object P therebetween, and driven to rotate together as paired devices around the oral cavity. However, the rotation is not a rotation to draw a simple circle, and the pair of the X-ray tube 31 and the detector 32 is driven such that the rotation center RC of the pair traces a given chevron-shaped orbit consisting of two connected arcs inside an approximately horseshoe-shaped tooth row, as shown in FIG. 2. This given orbit is an orbit previously designed to enable the X-ray to focus on a section taken along a standard shape and size of the tooth row in the oral cavity (hereinafter, such a section is referred to as a 3D reference tomographic plane SS) and trace the 3D referential tomographic plane SS. When the X-ray is focused to trace the 3D referential tomographic plane SS, the X-ray tube 31 and the detector 32 are not always rotate at an equal angular speed to the 3D referential tomographic plane SS. This rotation can be a rotation referred to as "movement along the tooth row", in which the angular speed is changed arbitrarily during the rotation.

It is necessary that the X-ray tube 31 and the detector 32 should be moved to be opposed to each other and keep the oral cavity of the object P located between such devices. However this opposed attitude does not always require the X-ray tube 31 and the detector 32 to be directly opposed to each other. Depending on how to design the apparatus, the X-ray tube 31 and the detector 32 rotate independently of each other and, though the oral cavity of the object P should be located therebetween, the X-ray is radiated obliquely to the object.

The 3D referential tomographic plane SS presents an approximately horseshoe-shaped trajectory on the X-Y plane, i.e., when being viewed in the Z-axis direction, as described, and an example of such a trajectory is shown in FIG. 2. The trajectory of this 3D referential tomographic plane SS is also known from, for example, a paper "R. Molteni, "A universal test phantom for dental panoramic radiography," MedicaMudi, vol. 36, no. 3, 1991." The X-ray tube 31, the 3D referential tomographic plane SS, the detector 32, a rotation axis AXz, and the rotation center RC through which the rotation axis AXz passes have a geometrical positional relationship shown in FIG. 3.

The 3D referential tomographic plane SS is parallel with the incident window of the detector 32 (the window is an X-ray detecting plane Ldet: refer to FIG. 6) and is a section curved along the Z-axis direction. This plane SS is defined as an elongated rectangular section when being developed two-dimensionally.

Figure 4:
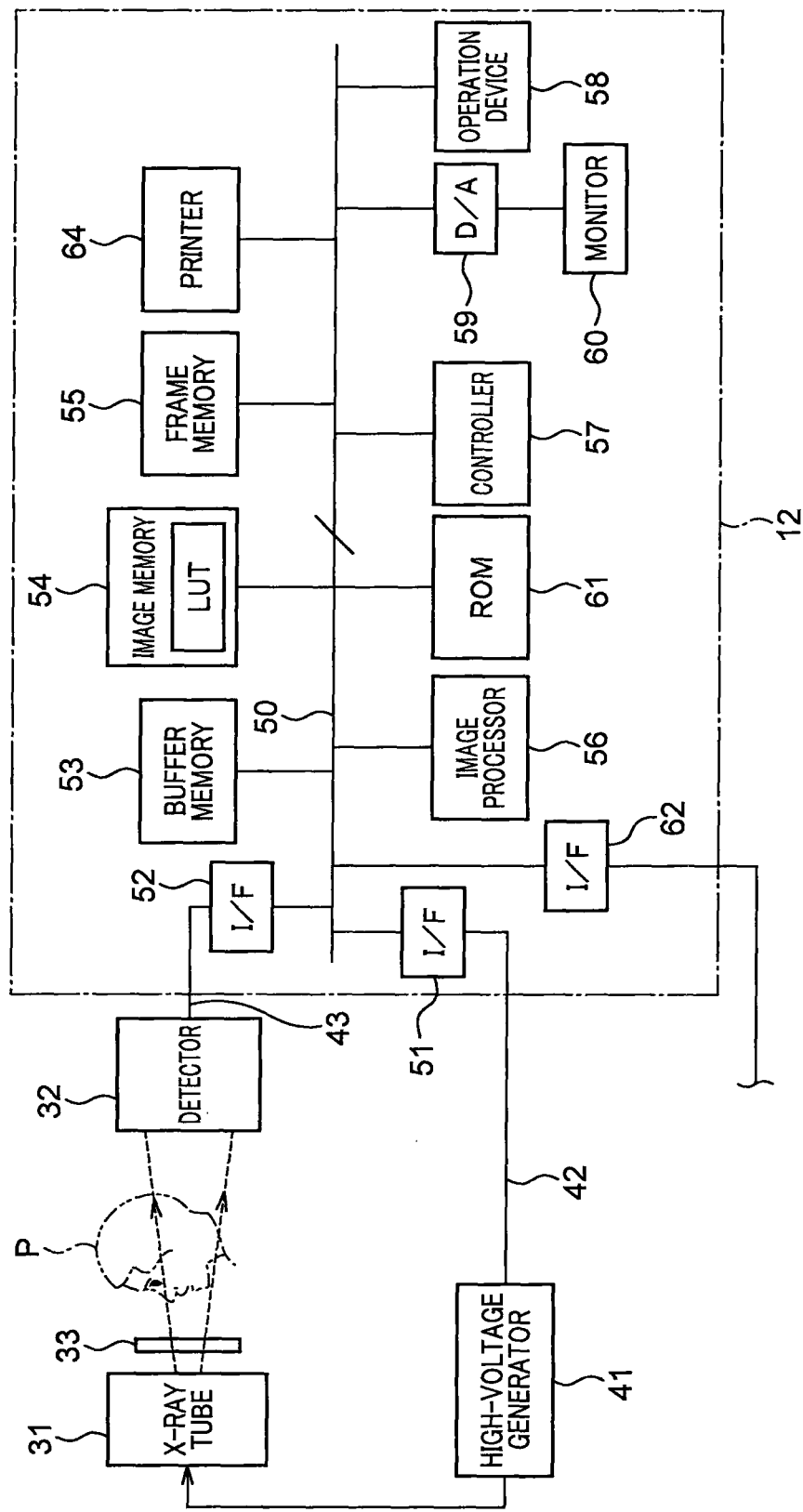
FIG. 4 is a block diagram outlining the electrical and electronic configuration of the panoramic imaging apparatus.

FIG. 4 shows an electric block form for control and processing performed by this panoramic imaging apparatus. As shown in the figure, the X-ray tube 31 is connected to the control & calculation apparatus 12 via a high-voltage generator 41 and a communication line 42. The detector 32 is connected to the control & calculation apparatus 12 via a communication line 43. The high-voltage generator 41 is arranged at the standing unit 13, the vertical movement unit 23, or the rotation unit 24 and responds to a control signal from the control & calculation apparatus 12 to be controlled according to X-ray radiation conditions such as a tube current and a tube voltage to the X-ray tube 31 and a timing sequence for the radiation.

The control & calculation apparatus 12 is required to process large amounts of image data, and is composed of for example a personal computer which is capable of storing large amounts of image data. The control & calculation apparatus 12 includes, as its essential components, interfaces 51, 52 and 62, a buffer memory 53, an image memory 54, a frame memory 55, an image processor 56, a controller (CPU) 57, and a D/A converter 59, which are mutually communicably connected via an internal bus 50. The controller 57 is communicably connected to an operation device 58, and the D/A converter 59 is also connected to a monitor 60.

Of the above components, the interfaces 51 and 52 are connected to the high-voltage generator 41 and the detector 32 respectively, and responsible for conducting communication on control information and acquired data transmitted from/to the controller 57 to/from the high-voltage generator 41 and detector 32. The other interface 62 connects the internal bus 50 and the communication line, which allows the controller 57 to be communicable with an external apparatus. It is therefore possible that the controller 57 takes in oral images acquired by an external oral X-ray imaging apparatus and outputs panoramic images acquired by the present apparatus, to an external server based on for example DICOM (Digital Imaging and Communications in Medicine) protocol.

The buffer memory 53 temporarily stores digital-quantity frame data received from the detector 32 via the interface 52.

The image processor 56, which is under the control of the controller 57, has functions of producing panoramic images of a predetermined 3D referential tomographic plane provided by the apparatus itself and performing post-processes to utilize the panoramic images in an iterative manner with an operator. Programs for realizing such functions are stored in the ROM 61 in advance. Hence, the ROM 61 serves as a recording medium in which programs according to the present invention are stored. While such programs can be stored in the ROM 61 in advance as stated above, they can be installed into recording mediums such as a not-shown RAM, via a communication line or a portable memory from an external system in some cases.

In the present embodiment, the 3D referential tomographic plane is prepared previously by the apparatus. Alternatively, the 3D referential tomographic plane may be provided by selecting a desired one from plural tomographic planes prepared previously by the apparatus before performing imaging. In other words, the 3D referential tomographic plane is a fixed section in the imaging space, but the foregoing selection allows the plane to be movably positioned in a limited amount of range in the depth (back-and-forth) direction of a tooth row.

Frame data processed by the image processor 56 and image data are stored in the image memory 54 in a readable and writable manner. The image memory 54 is composed of for example a large-capacity recording medium such as a hard disc (nonvolatile and readable and writable). The frame memory 55 is used to display image data such as panoramic image data reconstructed and panoramic imager data to be post-processed. The image data being stored in the frame memory 55 are read at intervals from the D/A converter 59 to be converted into corresponding analog signals, and displayed on the monitor 60.

The controller 57 controls the operations of all the components of the apparatus based on programs for control and processing, which are previously stored in the ROM 61. The programs are set such that the controller receives interactively information showing operator's operations for respective control items. Hence, the controller 57 is able to command acquisition (scanning) of frame data or other operations, as will be described later.

As shown in FIG. 1, a patient poses in a standing position or a seated position with his or her chin seated on the chin rest 25, his or her mouth biting the bite block 26, and his or her head touched to a head rest 28. This allows the patient's head (jaw) to be fixed positioned in an approximately central part in the space in which the rotation unit 24 rotates. With this patient's fixed posture, under the control of the controller 57, the rotation unit 24 rotates around the patient's head along the X-Y plane and/or an oblique plane to the X-Y plane (refer to arrows shown in FIG. 1).

During the rotation, under the control of the controller 57, the high-voltage generator 41 supplies to the X-ray tube 31 a pulse-mode high voltage (designated tube voltage and tube current) at intervals, whereby the X-ray tube 31 is driven on the pulse mode. This allows the X-ray tube 31 to radiate pulsed X-rays at intervals. The X-rays are transmitted through the patient's jaw (including the tooth row portion) positioned at the designated imaging position) and enters the detector 32. Responsively to this, the detector 32 detects the incident X-rays at a very fast frame rate (for example 300 fps) as described, and outputs in sequence, frame by frame, corresponding electric-quantity two-dimensional frame data (for example 64×1500 pixels). The outputted frame data are transmitted to the buffer memory 53 via the communication line 43 and the interface 52 in the control & calculation apparatus 12 for temporal storage therein. The frame data in the buffer memory are then transferred to the image memory 53 for storage therein.

Hence, the image processor 56 is configured to reconstruct (produce), as a panoramic image (a referential panoramic image), a tomographic image that focuses on the 3D referential tomographic plane SS using the frame data stored in the image memory 53. That is, this referential panoramic image is defined as "a panoramic image obtained under an assumption that a tooth row is present at and along the 3D referential tomographic plane SS." In addition, the image processor 56 uses this referential panoramic image to produce a three-dimensional (3D) referential image and a three dimensional (3D) autofocus image. This processing is outlined in FIG. 5. The 3D referential image is defined as "a three-dimensional image obtained under an assumption that a tooth row is present at and long the 3D referential tomographic plane SS." The 3D autofocus image is "a surface image automatically optimally focused on the tooth row", which is produced from the 3D referential image using frame data or data of the referential panoramic image. In other words, the 3D autofocus image is an optimally focused image with less blur, where the real position and actual size of a tooth row is depicted with higher precision.

In particular, it can be said that the 3D autofocus image takes into consideration that 3D autofocus images of individual persons differ person by person in most cases. In practice, it is very rare to find that tooth rows of individual persons being imaged are at and along the 3D referential tomographic plane SS (refer to FIG. 6). The tooth rows may partially or entirely offset from the 3D referential tomographic plane SS or may be oblique to that plane. In light of this, the 3D autofocus image is produced by automatically and accurately identifying the actual three-dimensional spatial position and shape of the tooth row of each person being imaged and automatically extracting from the identified results the actual shape of the person's tooth row.

Figure 3:
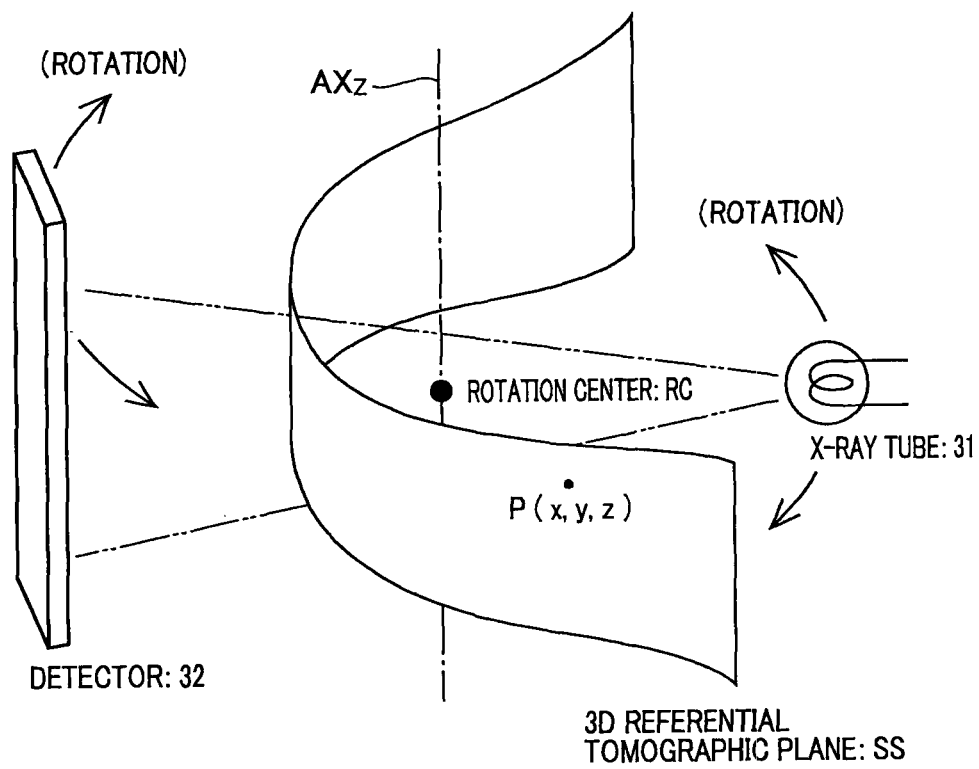
FIG. 3 is a perspective view explaining a geometry of the X-ray tube, the 3D referential tomographic plane, and the detector in the panoramic imaging apparatus.
Figure 6:
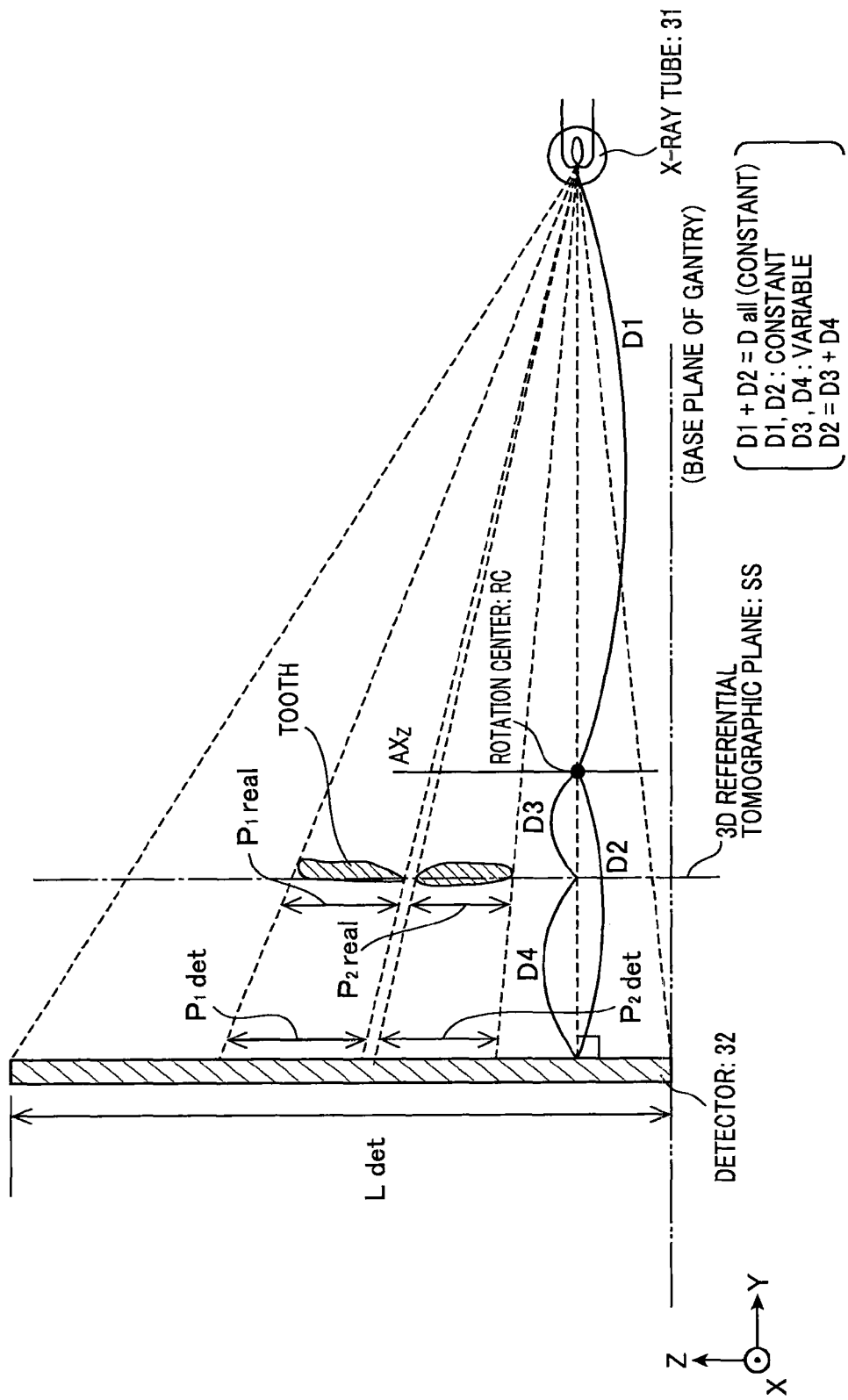
FIG. 6 is a view explaining a positional relationship among the X-ray tube, the 3D referential tomographic plane, the rotation center, and the detector.

The X-rays radiated from the X-ray tube 31 (serving as a point X-ray source) are transmitted through the oral cavity of an object P, and then are detected by the long detector 32 having a certain length in the X-axis direction. Hence, the radiated directions of the X-rays are oblique, as shown in FIGS. 3 and 6. Accordingly, there exists a ratio between the actual size of the tooth and the size of an image produced by the shade of the tooth projected onto the X-ray incident surface Ldet of the detector 32, and this ratio changes depending on positions of the rotation center RC. In the present embodiment, this ratio is called "an enlargement factor." In the example shown in FIG. 6 (only the height of the tooth is explained), a ratio between the actual height $P1_{real}$ of the tooth and the height $P1_{det}$ on the X-ray incident surface Ldet changes depending on positions of the rotation center RC. As exemplified in FIG. 2, the rotation center RC takes various positions, which change during one scan (data acquisition). An orbit on which the positions trace is set previously. The reason for the orbit is follows. As shown in FIG. 6, a distance DaII between the X-ray tube 31 and the detector 32 is kept unchanged, and distances D1 and D2 from the rotation center RC to the X-ray tube 31 and the detector 32 respectively are also kept unchanged. Meanwhile, for scanning with focusing on the 3D referential tomographic plane SS, design is made such that, during one to scan (data acquisition), the orbit traced by the positions of the rotation center RC changes to depict, by way of example, the shape of a mountain (refer to FIG. 2) to the horseshoe-shaped curved tooth row. Incidentally the orbit of the rotation center RC may be designed linearly or approximately linearly.

Concretely, a distance D3 from the rotation center RC to the 3D referential tomographic plane SS and a distance D4 (D3+D4=D2) from the detector 32 to the 3D referential tomographic plane SS change depending on advancement of the scanning. Depending on these changes, the rotation center RC comes closer to recedes from the tooth row, so that the X-ray tube 31 comes closer to or recedes from the tooth row as well. Since the X-ray tube 31 has an X-ray course which can be regarded as a point source, the size of a projection image onto the detection surface Ldet becomes bigger as the X-ray tube 31 comes closer to the tooth row even under a condition where the height of the tooth is the same. That is, the enlargement factor becomes larger in such a case. In the example shown in FIG. 2, compared with a case where the molar teeth (the back-tooth side) are scanned, scanning the anterior teeth allows the rotation center RC to come closer to the tooth row, providing the enlargement factor with larger amounts depending on how much closer to the tooth row. For example, in the case of FIG. 2, the distance d1 is given when one of the anterior teeth is scanned in an X-ray radiation direction of 0 degrees for example. Meanwhile, in the case of scanning some of the molar teeth, there are provided distances d2 and d3 in the X-ray radiation directions of 60 degrees and 75 degrees respectively, for example. In this example, there are provided relationships of d1<d2, d1<d3, and d2<d3. Although the trajectory of the rotation center RC shown in FIG. 2 is simply an example, it is always true that the rotation center RC comes closer to and then gets away from the tooth row when scanning is made to focus on the 3D referential tomographic plane SS by the panoramic imaging apparatus.

In such a case, the enlargement factor changes depending on what part of the tooth row is scanned. This fact becomes a significant barrier in an attempt at quantitatively analyzing changes in the structure and/or the temporal changes of the oral cavity.

In addition, though the above issue about the enlargement factor has been described on an assumption that the tooth row is present along the 3D referential tomographic plane SS, it is almost certain that such an assumption is not true. In effect, it is mostly correct that patients' tooth rows are shifted entirely or partially from the 3D referential tomographic plane SS. Thus the imaging should consider this fact.

The conventional panoramic images are produced with no consideration of the issues due to changes in the foregoing enlargement factor and shifts of tooth rows from the 3D referential tomographic plane SS. Thus, it is very difficult to quantitatively analyze the structure from the conventional panoramic images. In this regard, it is desired to provide a panoramic imaging apparatus capable of imaging objects with accuracy even when tooth rows are different in shapes and/or positions every object, and/or regardless of what part of the same object' tooth row is imaged.

With consideration this, the panoramic imaging apparatus according to the present embodiment has a feature that image distortion due to differences in the enlargement factor even for the same tooth row can be removed, part by part, and it is possible to automatically and accurately identify a three-dimensional spatial real position (including a shape) of a patient' tooth row. Thus it is possible to provide three-dimensional panoramic images with higher identification accuracy of positions (shapes), than has been provided in the past.

In the present embodiment, a tomosynthesis technique (simply called tomosynthesis) is used to obtain images of tomographic planes or sections of an object. Practically, of frame data (sets of pixel data) acquired at intervals by scanning, a plurality of frame data relating to individual positions of a trajectory of the 3D referential tomographic plane obtained by projecting the 3D referential tomographic plane to the X-Y plane are selected. Such selected frame data are shifted to be overlapped with each other depending on their positions and added with each other (shift & add). Hence, an "optimal focus" referred to in the present embodiment means that "being best focused, being less defocused", which also means that a region of interest in an image is higher in resolution than other regions thereof or an entire image has a higher degree of resolution.

When a referential panoramic image is produced, data composing this image are stored in the image memory 54 and also displayed by the monitor 60 in an appropriate display mode. The display mode is decided by an operator's intention which is given through the operation device 58.

(Image Processing)

Figure 5:
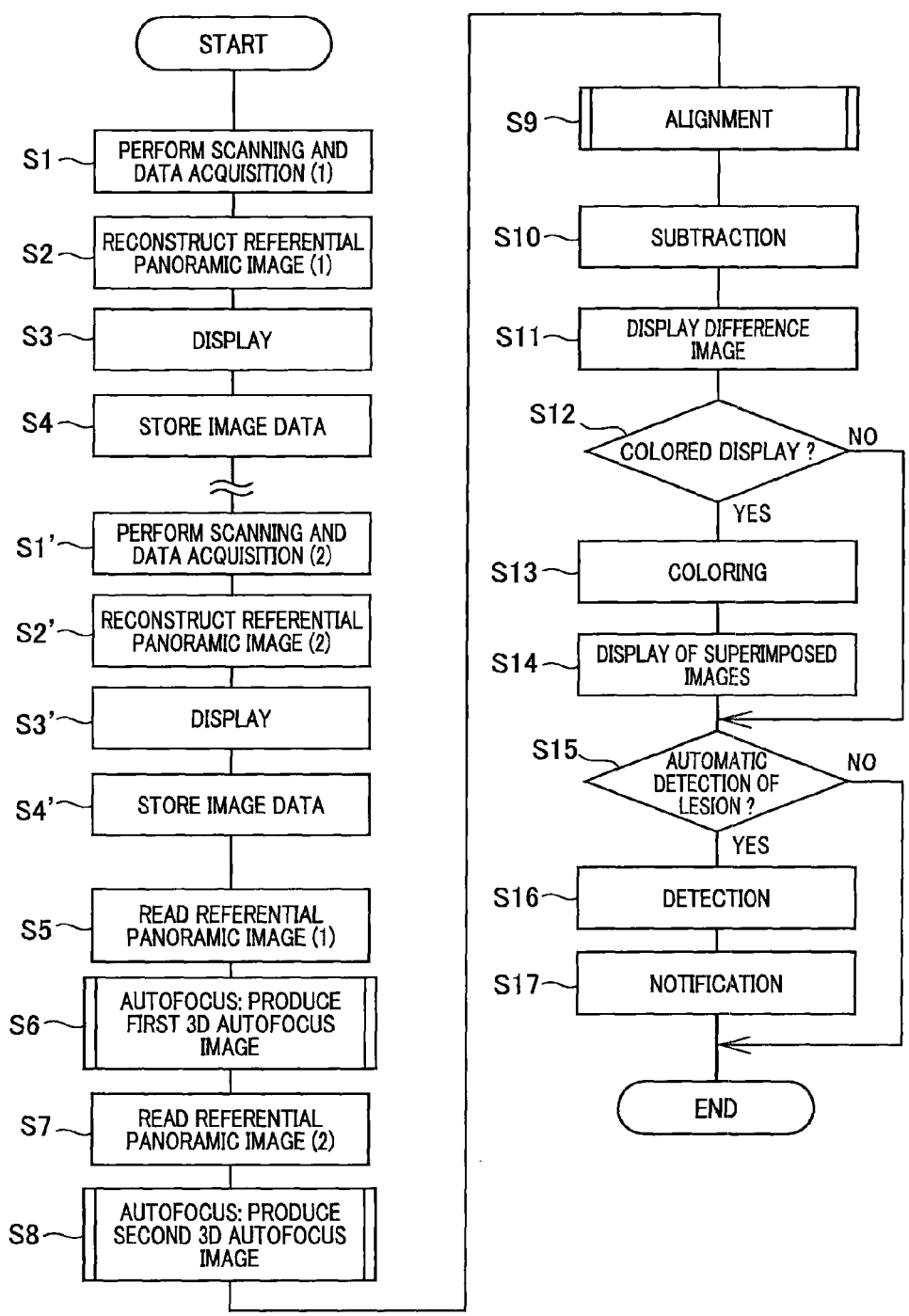
FIG. 5 is a flowchart showing an outline of processing for imaging performed cooperatively by a controller and an image processor provided in the panoramic imaging apparatus.

Referring to FIG. 5, processing performed cooperatively by the controller 57 and the image processor 56 will now be described. This processing includes, as described before, data acquisition by scanning, reconstruction of a referential panoramic image which is a pre-process, production of 3D autofocus image (surface image) which is one of the main processes, evaluation of spatial and temporal changes between two 3D autofocus images imaged at different timing points which is another of the main processes, and presentation of results of the evaluation.

<Data Acquisition and Reconstruction of Referential Panoramic Image>

First, the controller 57 responds to operator's instructions given via the operation device 58 to command scanning for the first data acquisition, after preparatory work such as positioning of a object (patient) P has been completed (step S1). This imaging time point is defined as T1.

In response to this command, the rotary drive mechanism 30A, the movement mechanism 30B, and the high-voltage generator 41 start to be driven according to a predetermined control sequence. As a result, during rotation of the pair of the X-ray tube 31 and the detector 32 around the jaw of the object P, the X-ray tube 31 radiates a pulsed X-ray or a continuous-wave X-ray at intervals or continuously. As described before, the pair of the X-ray tube 31 and the detector 32 is driven to rotate under a given drive condition so as to optimally focus on the 3D referential tomographic plane SS (refer to FIG. 6). The X-rays radiated from the X-ray tube 31 are transmitted through the object P to be detected by the detector 32. Accordingly, the detector 32 outputs, for example, at a rate of 300 fps, digital-quantity frame data (i.e., pixel data) in which amounts of X-ray transmission are reflected. The outputted frame data are temporarily stored in the buffer memory 53.

After the command for the scanning, the next command for the processing is provided to the image processor 56. The image processor 56 reconstructs a referential panoramic image PIst based on the shift & add process based on the tomosynthesis technique according to the spatial positions of the 3D referential tomographic plane SS, and the respective pixel values of the reconstructed image are stored (step S2). In this reconstruction process, the reconstructed image is multiplied by coefficients such that, similarly to the conventional situation longitudinal and lateral enlargement factors at the center of the anterior teeth become equal to each other.

Figure 7:
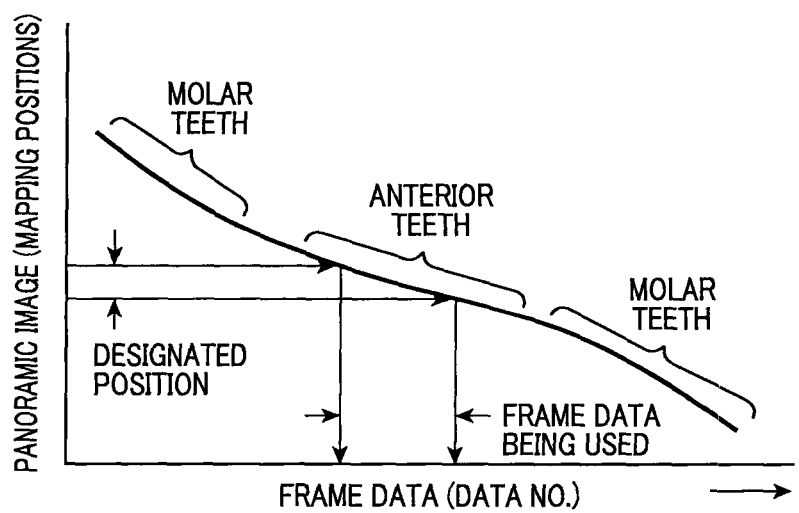
FIG. 7 is a graph explaining a relationship between frame data and mapping positions of the frame data to produce a panoramic image.

Although how to reconstruct an image is known, this will now be described a little. A set of frame data used for the reconstruction is obtained from a mapping characteristic which shows, as shown in FIG. 7 for example, mapping positions in the lateral direction of a panoramic image and a set of frame data which will be subjected to mutual addition for producing an image at the mapping positions. A curve showing this mapping characteristic consists of two curved portions which are steeper depending on molar teeth on both sides in the frame data direction (abscissa axis) and a curved portion which is gentler than those of the two curved portions for the molar teeth depending on the anterior teeth. As shown, in this projection characteristic is used to designate a desired mapping position in the lateral direction of the panoramic image. Based on this designation, the set of frame data used to produce an image at the designated mapping position and amounts of shift (i.e. degrees of overlapping necessary frame data, which is a gradient of the curve) are designated. The designated frame data (i.e, pixel values) are shifted in accordance with the designated shift amounts to be overlapped on one another and added to each other, thus providing data of a longitudinally extending image at the designated mapping position. By repeating the designation of mapping positions and shift & add calculation through the entire range in the lateral direction of the panoramic image, it is possible to reconstruct the first referential panoramic image PIst-1 which focuses on the 3D referential tomographic plane SS.

Figure 8:
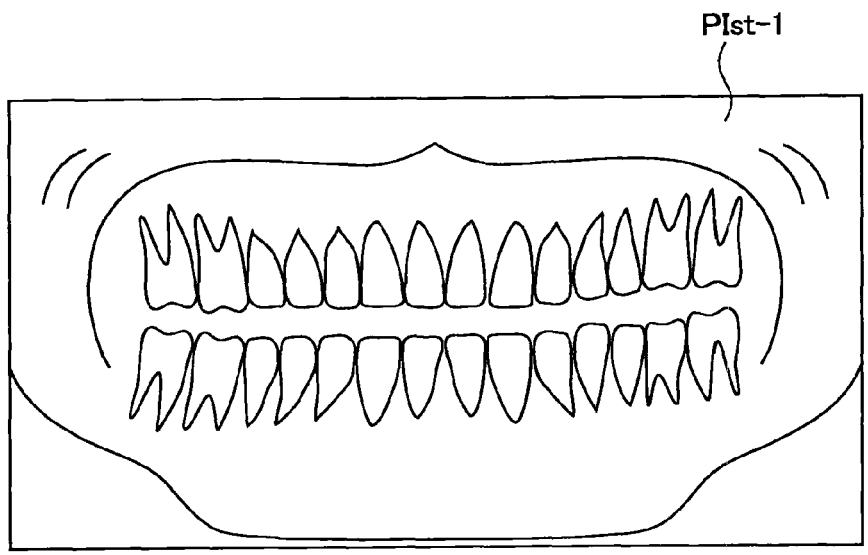
FIG. 8 is a view pictorially showing an example of a first referential panoramic image.

The image processor 56 then displays the produced first referential panoramic image PIst-1 on the monitor 60 (step S3), of which example is pictorially shown in FIG. 8. The pixel value data of the first referential panoramic image PIst-1 is stored in the image memory 54, for example (step S4).

Since the first referential panoramic image PIst-1 is an image produced by shifting the frame data to be overlapped on one another and mutually adding them, this image is two-dimensionally rectangular. Longitudinal and lateral distortion at the anterior teeth in this image PIst-1, which is due to a difference of the enlargement factor in the longitudinal and lateral direction, is improved to some extent similarly to the conventional, because the image is multiplied by the coefficients so as to make the longitudinal and lateral enlargement factors equal to each other at the center of the anterior teeth. However, as advancing to and through the to molar teeth, the longitudinal and lateral ratios of teeth become shifted from the correct ones. That is, the molar teeth are depicted to be less in size than the real size thereof. In many conventional cases, doctors are obliged to tolerate such panoramic images with distortion.

Figure 9:
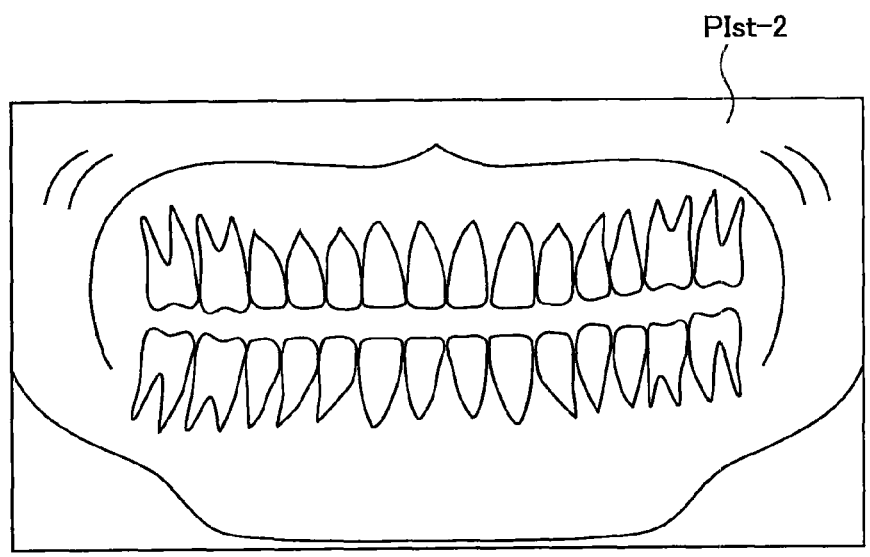
FIG. 9 is a view pictorially showing a second referential panoramic image.

Similarly to the above, the second scanning and data acquisition from the same patient (object) P are performed at a second imaging time point T2 which has elapsed, for example, two weeks from the first imaging time point T1. At this timing, processes of steps S1'-S4' which are equivalent to the foregoing steps S1-S4 are also performed in sequence. As a result, the second referential panoramic image PIst-2 is reconstructed and displayed as shown in FIG. 9, and its pixel value data are stored, for example, in the image memory 54.

(Production of 3D Autofocus Images)

The image processor 54 produces two 3D autofocus images at the foregoing first and second imaging timing points (times) T1 and T2.

(Production of the First 3D Autofocus Image)

Practically, the image processor 54 reads the image data of the first referential panoramic image PIst-1 from the image memory 54 to its work area (step S5). The image processor 54 then uses the read image data of the first referential panoramic image PIst-1 to produce a 3D autofocus image at the first imaging time point (step S6). This production is also one of the features of the present invention, and is a process for automatically identifying the actual position and shape of a tooth row. This identifying process also corrects distortion in the size of the tooth row, which results from that the X-ray radiation directions are oblique. This production will now be detailed.

Figure 10:
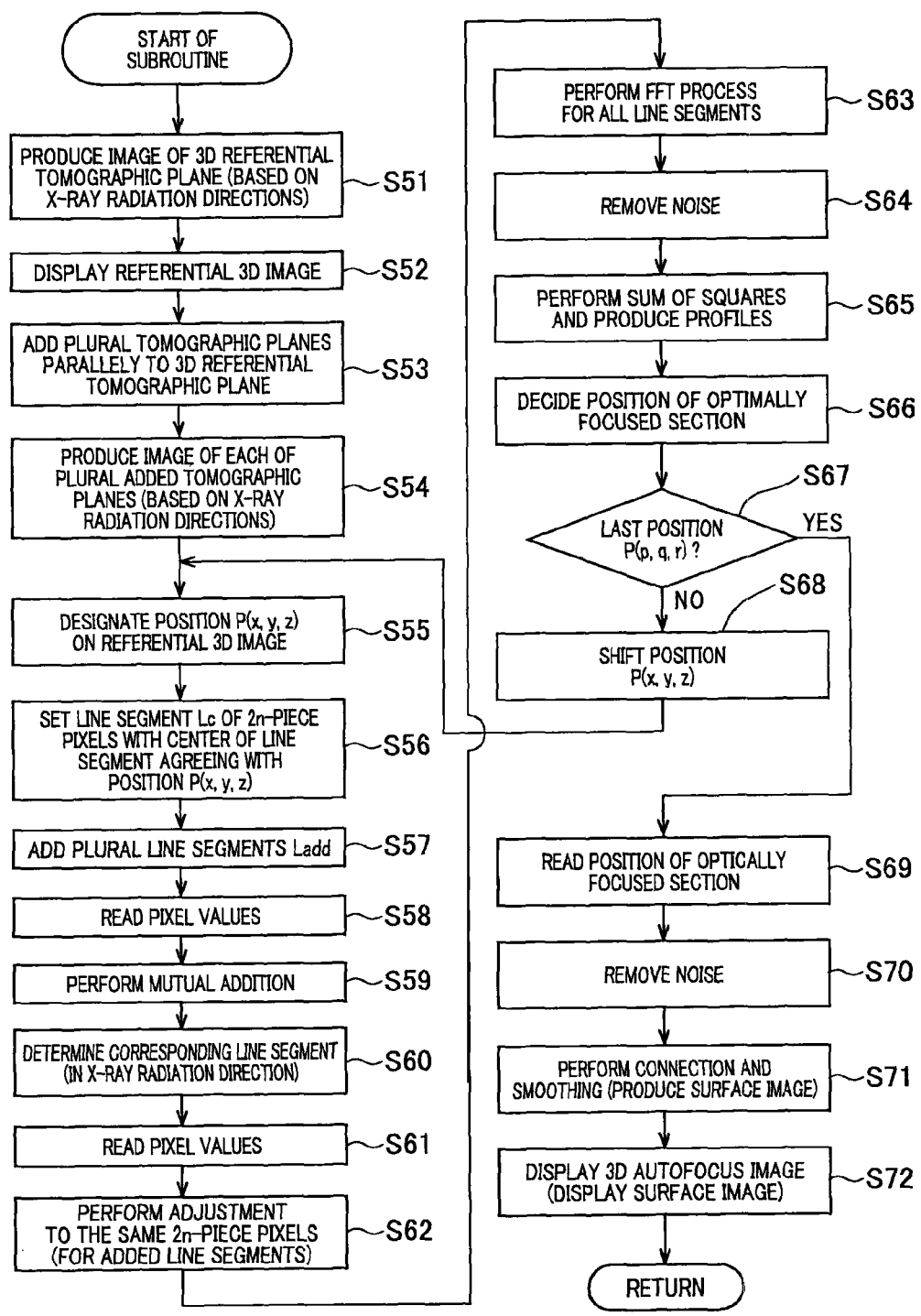
FIG. 10 is a flowchart outlining a process to identify the real positions and shapes of teeth, which is performed by an image processor.

A subroutine process for identifying the actually-existing position and shape of a tooth row is shown in FIG. 10. Incidentally this subroutine is also applied to the second referential panoramic image PIst-2, which will be described later. In the description of this subroutine, the reference marks for the first and second referential panoramic images PIst-1 and PIst-2 will be represented as "PIst".

First, the image processor 56 considers the X-ray radiation directions to produce an image along the 3D referential tomographic plane SS (Step S51). Concretely the referential panoramic image PIst (rectangular) is coordinate-converted to a curved plane parallel with the 3D referential tomographic plane SS (a curved plane) to produce a 3D panoramic image along the coordinate-converted curved plane. Each of the pixels of the this 3D panoramic image is projected to the 3D referential tomographic plane SS along each of the X-ray radiation directions DRx. This projection is performed using frame data obtained by calculating changes of tomographic planes and coordinate-converting the obtained frame data. This provides a projection image along the curved 3D referential tomographic plane SS. The pixel values of this projection image are stored in the image memory 54.

Figure 11:
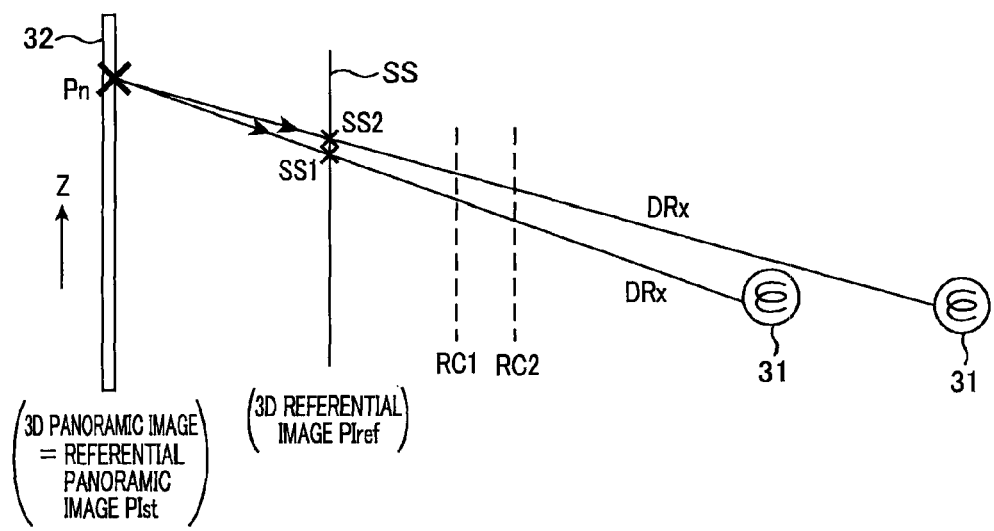
FIG. 11 is a view explaining a difference between angles from the same position in the Z-axis direction on a 3D panoramic image to the X-ray tube, which angles are caused by positional changes in the rotation center of the pair of the X-ray tube and the detector.

The projection is performed, as shown in FIG. 11, along each of the oblique projection directions directed to the rotation center RC (RC1, RC2), that is, the position where the X-ray tube 31 is present. When referring to the example in FIG. 11, a pixel located at a position Pn in the height direction (the Z-axis direction) of the 3D panoramic image will be projected to different positions SS1 and SS2 on the image of the 3D referential tomographic image SS, which is due to differences of positions at each of which the X-ray tube 31 is located.

The projection image produced by this projection is called a 3D referential image PIref in the present embodiment. This 3D referential image PIref is produced by oblique projection with consideration of characteristics of the foregoing enlargement factor, in which the oblique projection is performed at each of the pixels of the referential panoramic image PIst. By this oblique projection, enlargement of teeth belonging to the anterior teeth, which have large enlargement factors, is corrected to have real sizes thereof, while enlargement of teeth belonging to the molar teeth on both sides of the tooth row, which have small enlargement factors, is also corrected to have real sizes thereof. Hence, in the 3D referential image PIref, the teeth are depicted with their real sizes and have no or less distortion which is due to the size of the enlargement factors caused by the moved rotation center RC during the scanning. However it should be noted that this 3D referential image PIref is produced on the assumption that the tooth row is present at and along the 3D referential tomographic plane SS. It is rare that actual teeth are present at and along the plane SS, so that it is required to perform further processing to identify the real spatial positions and shapes of the teeth.

Figure 12:
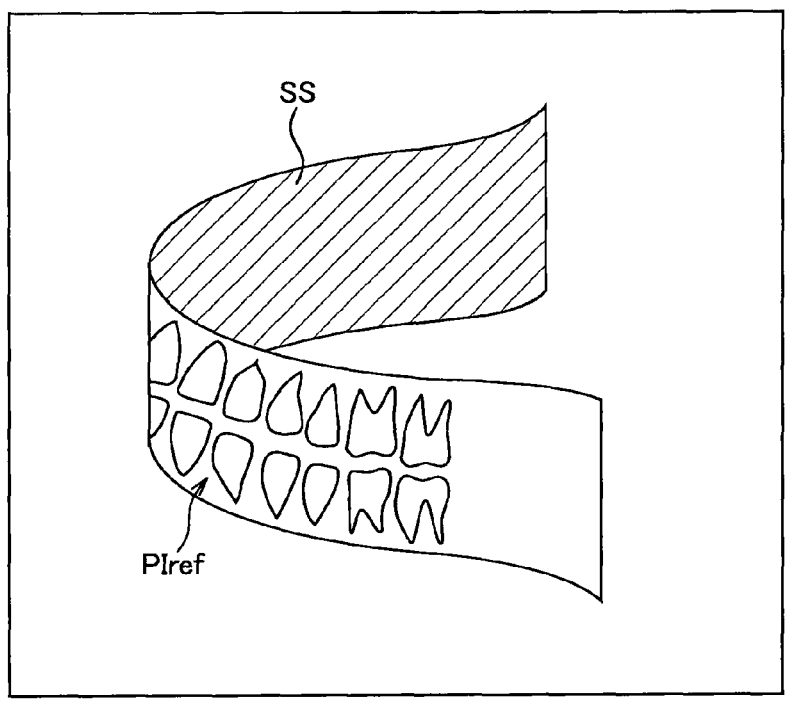
FIG. 12 is a view pictorially showing an example of a 3D reference image.

The image processor 56 displays the 3D referential image PIref on the monitor for operator's reference (step S52). This is shown in FIG. 12.

Figure 13:
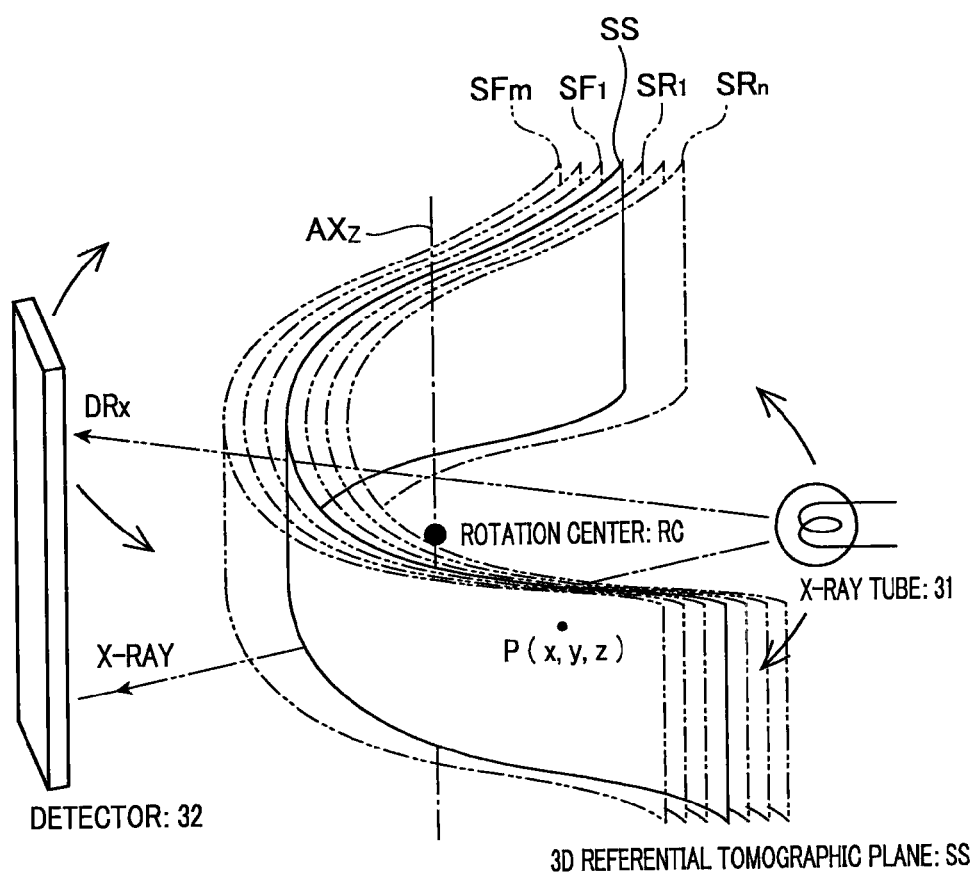
FIG. 13 is a perspective view explaining a plurality of parallel tomographic planes added to a 3D referential tomographic plane.
Figure 14:
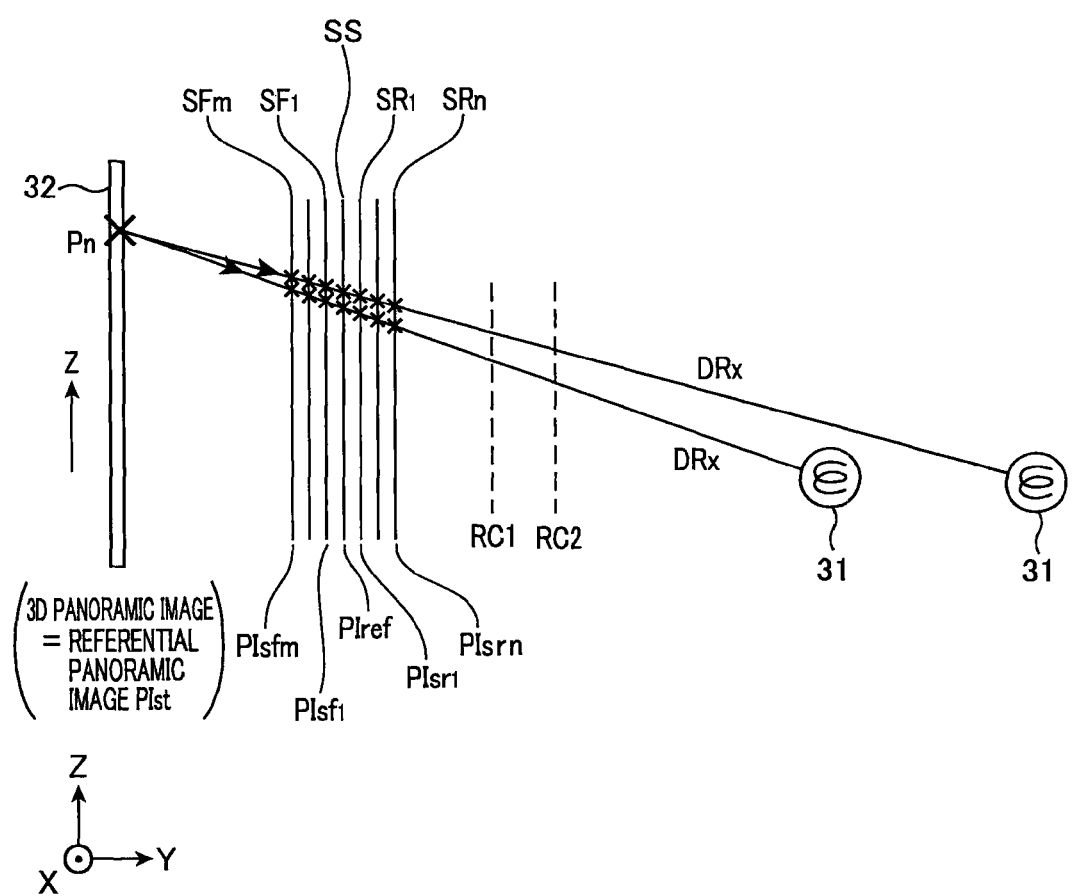
FIG. 14 is a view explaining differences of positions projected on the plurality of tomographic planes, which positions are obtained when the same Z-axial position on a 3D panoramic image is projected to the X-ray tube, wherein the positional differences are caused by positional changes in the rotation center of the pair of the X-ray tube and the detector.

The image processor 56 then adds a plurality of curved and parallel tomographic planes to the 3D referential tomographic plane SS (step S53). This is shown in FIG. 13. As shown, a plurality of tomographic planes are added to the 3D referential tomographic plane SS such that such tomographic planes are set before and after the plane SS respectively in the X-ray radiation directions DRx (i.e., the depth direction of the tooth row). By way of example, plural tomographic planes SFm-SF1 are located on the front side of the 3D referential tomographic plane SS at intervals of D1 (for example, 0.5 mm), while plural tomographic planes SR1-SRn are located on the rear side of the plane SS at intervals of D2 (for example, 0.5 mm). The intervals D1 and D2 may be equal to each other or different from each other. In addition, the number of tomographic planes to be added may be one on the front and rear sides of the plane SS respectively (i.e., m, n=1) or may be one or plural on either the front side or the rear side of the plane SS.

Incidentally, position data indicative of the virtually added tomographic planes SFm-SF1 and SR1-SRn are previously stored in the ROM 61 together with positional data of the 3D referential tomographic plane SS, so that the image processor 56 can perform the addition through reading of the positional data and loading them into a work area of the image processor 56. The heights of the tomographic planes SFm-SF1, SS, and SR1-SRn are decided appropriately in consideration of the maximum gradient of the X-ray radiation directions DRx and the height of the tooth row. Every time the identification processing is performed, the positions (the intervals D1, D2) of the tomographic planes to be added and the number thereof may be changed interactively.

Then, similarly to the process at step S51, with consideration of the angles of the X-ray radiation directions DRx, the image processor 56 projects the referential panoramic image PIst onto each of the tomographic planes SFm-SF1 and SR1-SRn by obtaining frame data through calculation of changes of tomographic planes and coordinate-changing the obtained frame data (step S54). As a result, images projected to the respective added tomographic planes SFm-SF1 and SR1-SRn are produced. The pixel values of such projection images are stored in the image memory 54.

In the present embodiment, the produced projection images are referred to as 3D added images PIsfm, . . . , PIsf1, PIsr1, . . . , PIsrn. Each of these 3D added images PIsfm, . . . , PIsf1, PIsr1, . . . , PIsrn is also produced by the oblique projections performed through the individual pixel positions of the referential panoramic image PIst, in which the oblique projections take into account of the foregoing differences in the enlargement factors. This is exemplified in FIG. 14, in which the same pixel existing at a position Pn in the height direction of a 3D panoramic image (i.e., the Z-axis direction) is projected onto different positions on the respective 3D added images PIsfm, . . . , PIsf1, PIsr1, . . . , PIsrn, which are due to differences in positions where the X-ray tube 31 is located.

Hence, the teeth depicted in the 3D added images PIsfm, . . . , PIsf1, PIsr1, . . . , PIsrn are depicted with their real sizes and distortion due to the variation of the enlargement factors, which is due to the movement of the rotation center RC during the scanning, is removed or suppressed from such 3D added images. It should be noted however that the 3D added images PIsfm, . . . , PIsf1, PIsr1, . . . , PIsrn are produced on the assumption that the tooth row is present at and along each of the 3D added images PIsfm, . . . , PIsf1, PIsr1, . . . , PIsrn.

As a modification, the plural 3D added images PIsfm, . . . , PIsf1, PIsr1, . . . , PIsrn thus produced can be displayed on the monitor 60 as three-dimensional images as they are or displayed on the monitor 60 as rectangular two-dimensional images produced through coordinate conversion.

Figure 15:
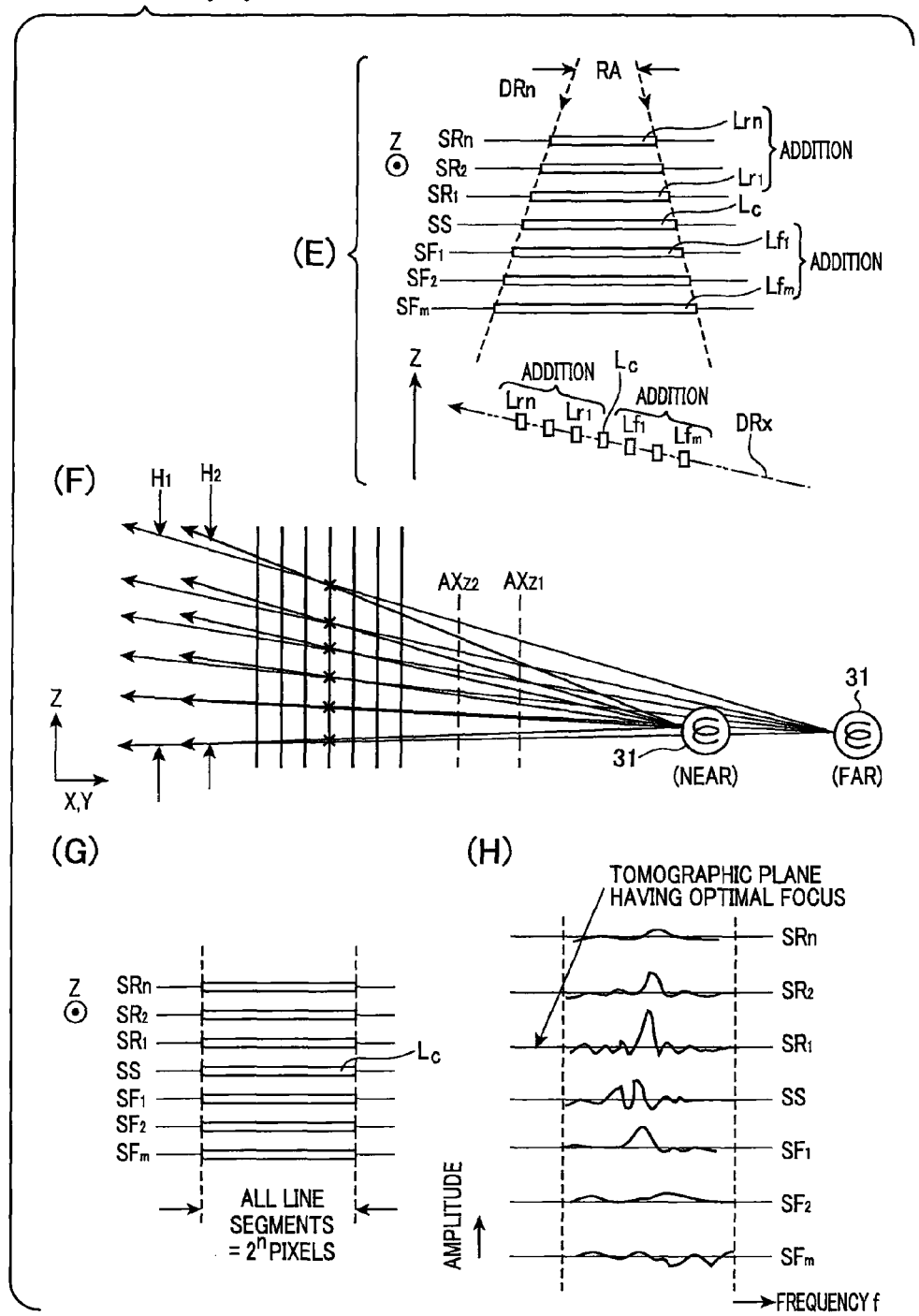
FIG. 15(1) is a view explaining, together with FIG. 15(2), the process to identify optimally-focused tomographic planes for each of positions on the 3D reference image.

The image processor 56 then designates an initial position P(x, y, z) on the 3D referential image PIref, that is, the 3D referential tomographic plane SS (step S55; refer to FIG. 15(A)). After this, the image processor designates a line segment Lc of a given length centering the designated position P(x, y, z) on the 3D referential image PIref (step S56; refer to FIG. 15 (B)). This line segment Lc has the given length corresponding to $2^n$ pieces (n=1, 2, 3, . . . ; for example 128 pieces). As modifications, the line segment Lc can be drawn along a part of the curved 3D referential tomographic plane SS so that the line segment is curved or can be drawn in a limited range regarded as being linear.

Then the image processor 56 virtually adds plural line segments Ladd on the upper and lower sides of the designated line segment Lc(x, y, z) on the image, respectively, in which the plural line segments Ladd have the same length as that of the line segment Lc(x, y, z) (step S57; refer to FIG. 15(C)).

Alternatively the processes of the foregoing steps S55-S57 may be performed on the two-dimensional plane of the referential panoramic image PIst.

The image processor then reads, from the image memory 54, the pixel values Pij of respective 2n-piece pixels composing each of the foregoing line segment L and plural line segments Ladd, and assigns the read pixel values to the respective line segments (step S58). The pixel values Pij have been already acquired and stored through the foregoing steps S51 and S54.

The image processor then mutually add the pixel values Pij of the pixels corresponding to the line segment L and line segments Ladd to obtain 2n-piece pixel values Pij* that composes the line segment Lc(x, y, z), the 2n-piece pixel values Pij* being for a frequency analysis (step S59; refer to FIG. 15(D)). This addition makes it possible to reduce statistical noise in a later-described frequency analysis of changes in the pixel values, even if the pixel values of the line segment L(x, y, z) originally contain the statistical noise.

Then, on each of the 3D added images PIsf1, . . . , PIsf1 and PIsr1, . . . , PIsrn, the image processor 56 calculates the spatial positions of the line segments Lfm-Lf1 and Lr1-Lrn that face the line segment Lc(x, y, z) designated currently on the foregoing 3D referential image PIref, in the X-ray radiation direction DRx passing through the currently designated position P(x, y, z) (step S60; refer to FIG. 15 (E)).

In this case, the current center position P(x, y, z) and the length of the line segment Lc, and the rotational positions of the X-ray tube 31 during the scanning are known. Hence, it is possible to calculate an X-ray radiation range RA which is fan-shaped when being viewed in the Z-axis direction, in which this range RA is formed by connecting each of both ends of the line segment Lc to the X-ray tube 31. As a result, as long as the position P(x, y, z) is designated, the spatial positions of the line segments Lfm, . . . , Lf1 and Lr1, . . . , Lrn limited by the X-ray radiation range in compliance with the designated position can also be designated by the image processor.

The process of step S60 to designate the position the position P(x, y, z) on the 3D referential image PIref is repeated until the same process for all the positions thereon is completed. Hence, in terms of effective X-ray radiation, the X-rays radiated from the X-ray tube 31 whose position comes near and farer transmit through the virtually set tomographic planes SFm-SF1, SS, and SR1-SRn within a range of H1 to H2 (a Z-axial range) in the fan shape (refer to FIG. 15 (F)). With consideration this fact, the tomographic planes SFm-SF1, SS and SR1-SRn themselves may be horseshoe-shaped sections having heights which change in every scanning direction and being parallel with each other.

When the line segments Lfm-Lf1 and Lr1-Lrn have been set as above, the image processor 56 reads pixel values Pij* of such line segments from the image memory 54 (step S61).

As shown in FIG. 15(E), since the X-ray tube 31 has a point X-ray source, the X-ray radiation range RA becomes a fan shape (when being viewed along the Z-axis direction). Hence, the pixels of each of the line segments Lfm-Lf1 and Lr1-Lrn are not 2n-pieces in number. Thus the image processor 56 multiplies each of the line segments Lfm-Lf1 and Lr1-Lrn by a coefficient depending on the distances D1 and D2 in such a manner that the number of pixels of each of the added line segments Lfm-Lf1 and Lr1-Lrn becomes equal to the number of pixels, 2n, of the referential line segment Lc(x, y, z). Accordingly, as pictorially shown in FIG. 15(G), all the line segments Lfm-Lf1, Lc and Lr1-Lrn are formed to be parallel with each other and to have the same number of pixels, 2n.

After this, the image processor 56 applies a frequency analysis to changes in the values of pixels of each of all the line segments Lf1-Lfm, Lc, and Lr1-Lrn (step S63). Thus, as shown in FIG. 15(H), as to the line segments Lfm-Lf1, L and Lr1-Lrn, there are provided analyzed results consisting of an abscissa axis showing frequencies and a vertical axis showing Fourier coefficients (amplitudes).

In the present embodiment, the frequency analysis is performed using fast Fourier transformation, but wavelet transformation may be adopted as such frequency analysis. Moreover, instead of such frequency analysis, a sobel filter to calculate the first derivation for edge extraction can be used for the equivalent process to the above. In using this filter, the position of a tomographic plane which provides an edge with a maximum filtered value can be regarded as an optimally focused position.

Figure 16:
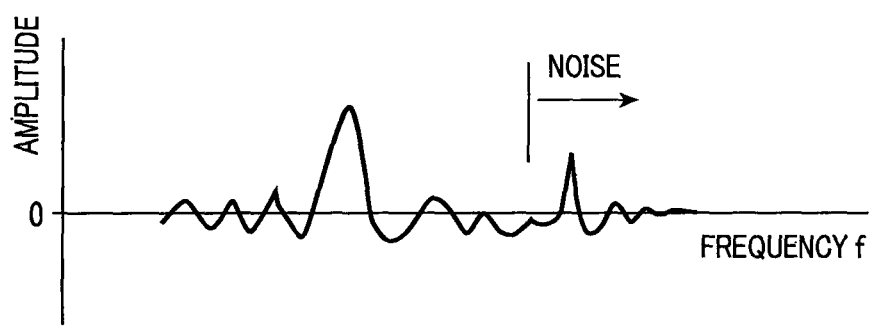
FIG. 16 is a graph exemplifying a frequency analysis result in an identification process for the optimally focused positions.
Figure 17:
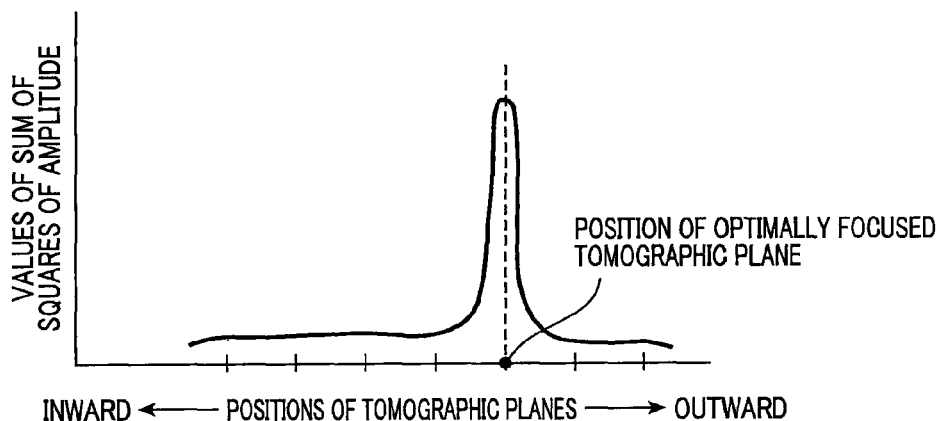
FIG. 17 is a graph exemplifying the position of an optimally focused tomographic plane obtained in the identification process for the optimally focused positions.

The image processor then removes noise from the frequency analyzed results for all the line segments Lf1-Lfm, Lc, and Lr1-Lrn (step S64). FIG. 16 exemplifies the frequency analyzed characteristic for one line segment. Coefficients of frequency components which belong to a given frequency range next to a maximum frequency of the analysis are removed, with coefficients of the remaining high-frequency components adopted. The reason for such removal is that frequency components which are present in the given frequency range next to the maximum frequency provide noise signal components.

Further the image processor 56 calculates sums of squares for the coefficients of the frequency analyzed characteristic of each of the line segments, and produces a profile having a vertical axis to which the values of sums of squires are assigned and an abscissa axis to which the positions of the respective tomographic planes SFm-SF1, SS, and SR1-SRn are assigned, where the X-ray radiation direction DRx passing through the initial position P(x, y, z)=P(0, 0, 0) passes through the positions of such tomographic planes (step S65). This profile is exemplified in FIG. 17. In this profile, the positions of the tomographic planes mean the positions the plural tomographic planes SF1-SFm, SS, and FR1-FRn in the X-ray radiation direction DRx (i.e., the depth direction of the tooth row).

Figure 18:
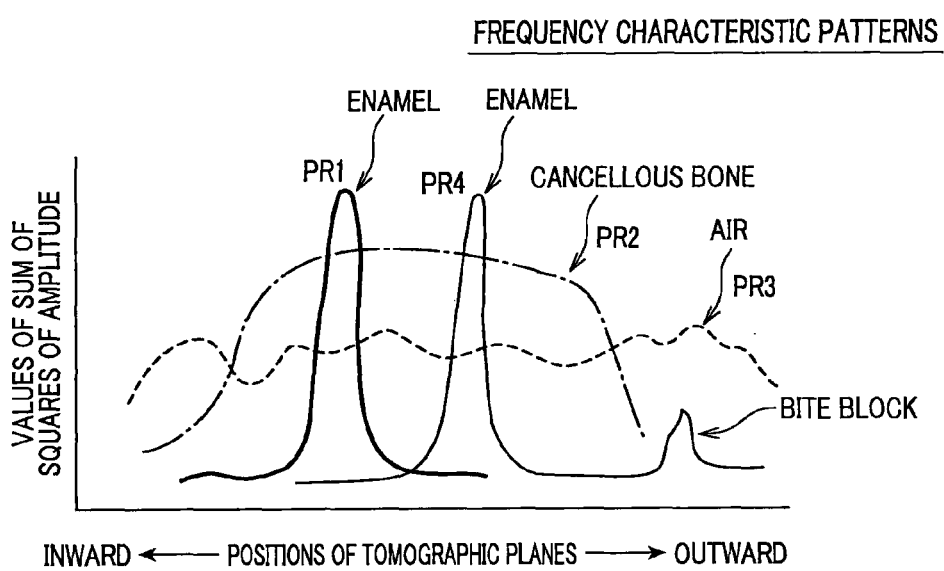
FIG. 18 is a graph exemplifying frequency characteristic patterns changing depending on tomographic plane positions.
Figure 19:
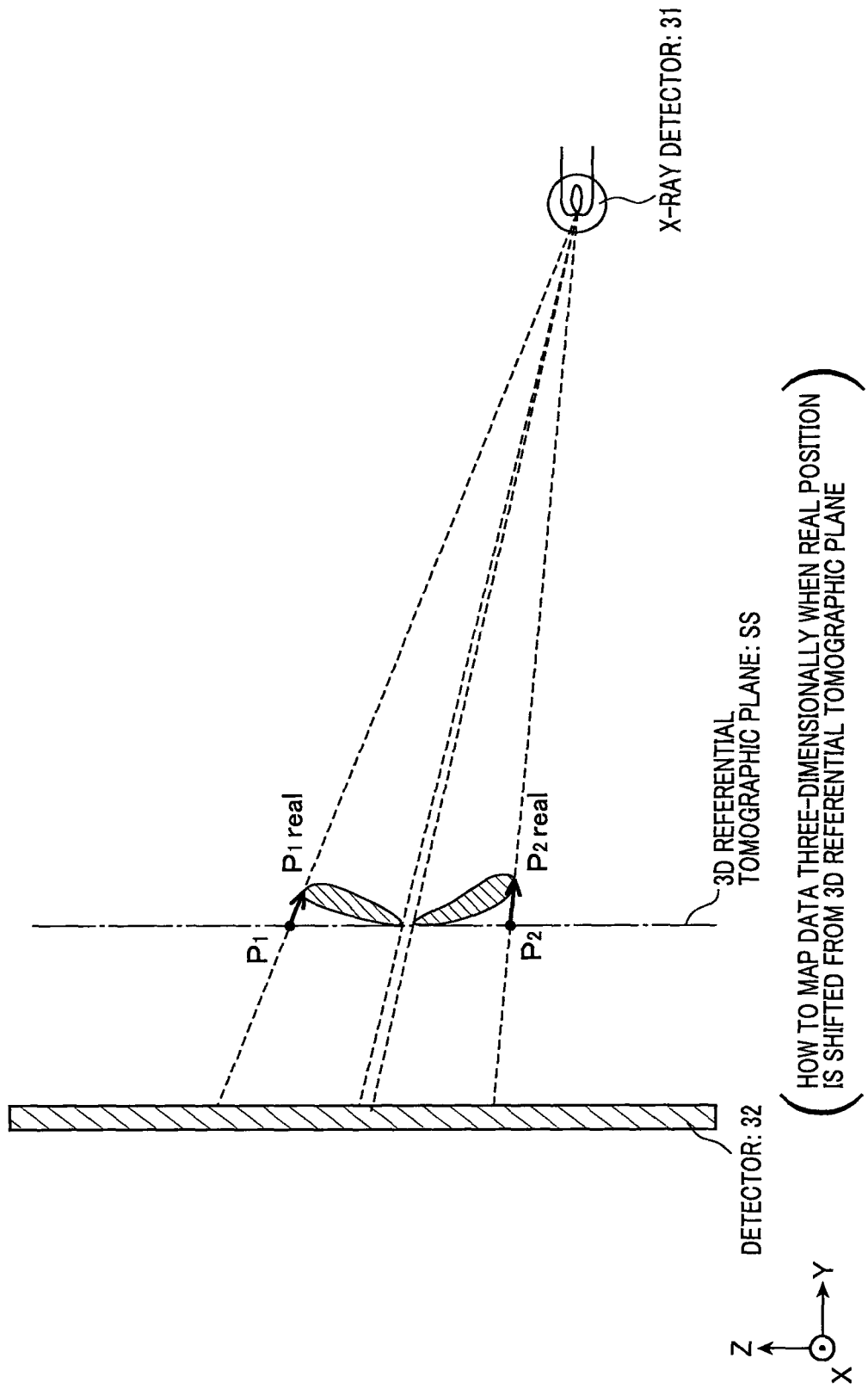
FIG. 19 is a view explaining a state where the real positions of teeth are deviated from the 3D referential tomographic plane.
Figure 20:
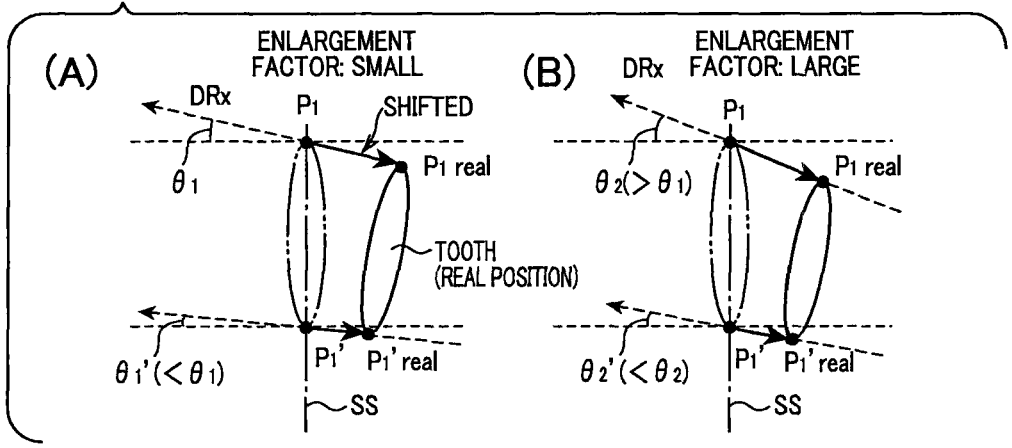
FIG. 20 is a view explaining a state where a tooth is shifted from the position of the 3D referential tomographic image to its real position depending on the size of an enlargement factor.
Figure 21:
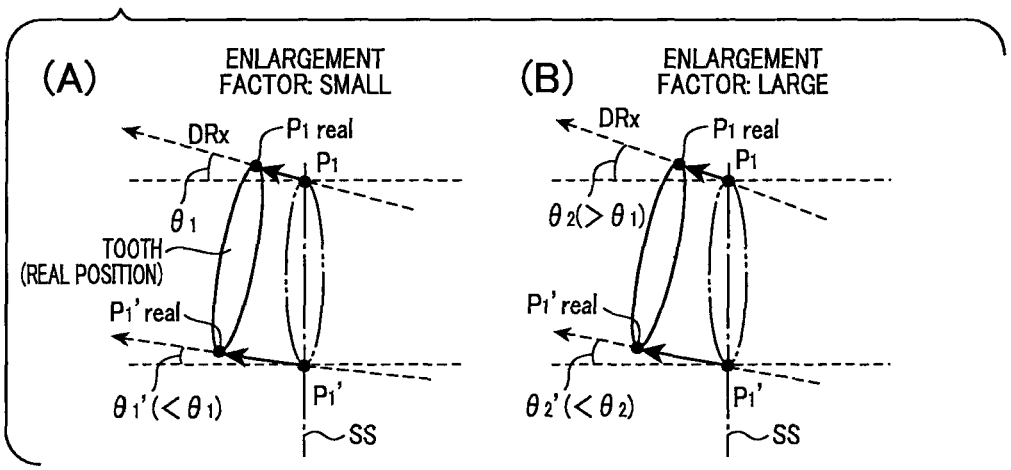
FIG. 21 is a view explaining a state where a tooth is shifted from the position of the 3D referential tomographic image to its real position depending on the size of an enlargement factor.

FIG. 18 exemplifies, as typical patterns, a plurality of types of profiles PR1, PR2, PR3 and PR4 respectively showing substances composed of enamel, cancellous bone, air and bite blocks. If there is a substance of enamel, i.e., tooth, anywhere in the X-ray radiation direction DRx that passes through the currently designated position P(x, y, z), the profile PR1 has a sharp peak. If there is cancellous bone in that X-ray radiation direction DRx, the profile PR2 has a gentle convex curve. Similarly, if there exists only air in that X-ray radiation direction DRx, the profile PR3 tends to show a curve having no specific peaks. Moreover, when the bite block is present in that X-ray radiation direction DRx, the profile PR4 exhibits two sharp peaks. Of such two peaks, one appearing inward (on the X-ray tube side) in the X-ray radiation direction DRx shows that the substance thereat is enamel, while the other appearing outward (on the detector side) shows that the substance thereat is the bite block. Data indicating the patterns of the profiles shown in FIG. 18 are previously stored, as reference profiles, in the ROM 61 in the form of a reference table.

Hence, the image processor 56 refers to the reference table to specify an optimum focused position of the tooth in the X-ray radiation direction DRx passing through the currently designated position P(x, y, z) (step S66).

That is, a pattern recognition technique is used to determine that the profile obtained in the last step S65 corresponds to which of the reference profiles PR1-PR4. First, when the obtained profile is the reference profile PR2 or PR4, such a profile is withdrawn from the consideration. In contrast, when the obtained profile corresponds to the reference profile PR1 (i.e., enamel), it is identified that the section position showing its peak, i.e., the position of any of the plural tomographic planes SF1-SFm, SS, FR1-FRn, is optimally focused. Moreover, when the obtained profile is fit to the reference profile PR4, it is also identified that an inward sectional position expressing a peak (a sectional position showing enamel on the X-ray tube side), in other words, the position of any of the plural tomographic planes SF1-SFm, SS, FR1-FRn, is optimally focused.

By the foregoing specifying steps, it is identified that a portion of the tooth depicted at the currently designated position P(x, y, z) is actually present at which position in the depth direction. In effect, a tooth portion depicted on the 3D referential image PIref along the 3D referential tomographic plane SS may be present on the front or rear sides of the plane SS. The real position of the tooth portion in the imaging space is specified precisely by the foregoing specifying steps. In other words, it can be understood that a tooth portion depicted on the 3D referential image PIref under the condition that the tooth portion is on and along the 3D referential tomographic plane SS is shifted to its real spatial position by the foregoing specifying steps.

Figure 22:
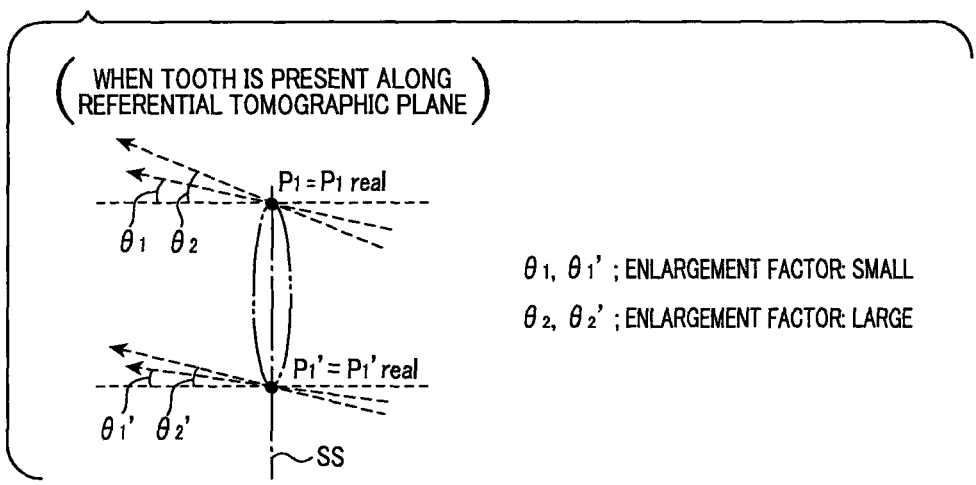
FIG. 22 is a view explaining a state where a tooth is shifted from the position of the 3D referential tomographic image to its real position depending on the size of an enlargement factor.

As a result, as shown in FIGS. 19-22, every time the position P(x, y, z) is designated, a position P1 on the 3D referential tomographic plane SS (i.e., in the 3D referential image PIref) is shifted to a position P1real (or a position P2 is shifted to a position P2real). In particular, the positions of the line segments Lfm-Lf1 and Lr1-Lrn which are set on the plural added tomographic planes SFm-SF1 and FR1-FRn are set in consideration of the oblique angle θ of each of the X-ray radiation directions DRx. Thus, the shifted position PIreal in the case of a smaller oblique angle θ (refer to FIGS. 20(A) and 21(A)) becomes lower in the Z-axis direction than in the case of a larger oblique angle θ (refer to FIGS. 20(B) and 20(B)). Accordingly, the shifted position PIreal can be compensated in distortion depending on the oblique X-ray radiation angle θ, i.e., the size of the enlargement factor. Incidentally as shown in FIG. 22, when the tooth is present at and along the 3D referential tomographic plane SS, a relationship of P1=PIreal is met. In this case, the 3D referential tomographic plane SS, at and along which it is assumed that the tooth is present, provides a real position, thus providing a shift amount of zero.

The image processor 56 then proceeds to step S65, at which data indicating the real position of the tooth portion is stored every position P(x, y, z) in the work area thereof.

In this way, as to the currently designated position P(x, y, z) on the 3D referential image PIref (i.e., the 3D referential tomographic plane SS), practically, as to the first designed initial position P(0, 0, 0), a specifying process is performed in the depth direction passing through the initial position P(0, 0, 0). As the specifying process, filtering is performed to check whether or not there is a portion of the tooth (enamel). And when it is checked that there is such a tooth portion, an optimally focused position for the tooth part is specified in the depth direction.

Figure 23:
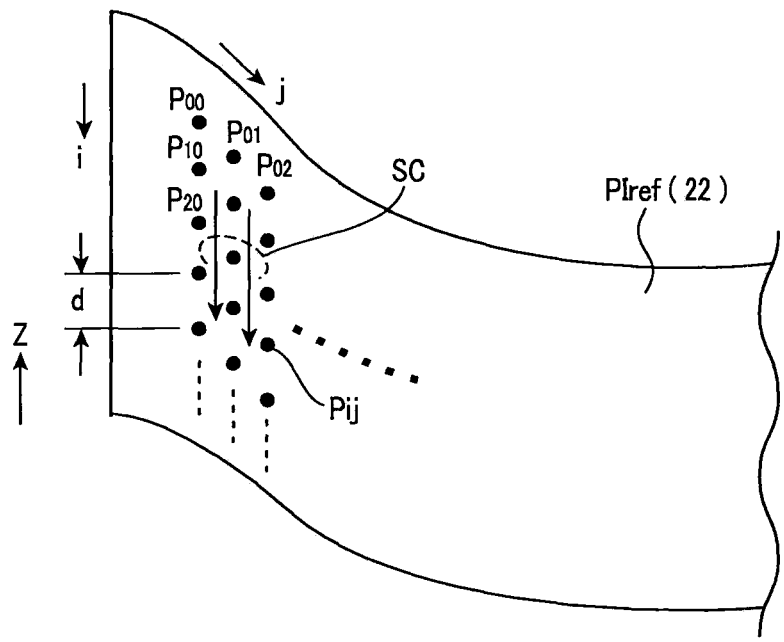
FIG. 23 is a perspective view explaining a process for moving processing points on the 3D reference image in order to perform the position identifying process.

After this, as shown in FIG. 23 for example, the image processor 56 determines whether or not the foregoing specifying steps have been completed at all determination points (sampling points) P previously set on the 3D referential image PIref (step S67). This determination is executed by checking whether or not the currently processed position P(x, y, z) is the last position P(p, q, r). If this determination is NO which shows the specifying steps have not been competed at all the determination points P, the image processor 56 shifts the determination point P(x, y, z) by one (step S68), before returning to the foregoing step S55 to repeat the foregoing series of specifying steps.

As shown in FIG. 23, the plural determination points P are previously mapped with given intervals on the 3D referential image PIref (i.e., the 3D referential tomographic plane SS). In the example shown here, along both the vertical direction i and the horizontal direction j of the 3D referential image PIref, the positions P are mapped at the same given intervals d in the vertical and horizontal directions. Alternatively, the intervals d may be differentiated between the vertical and horizontal directions i and j from each other. The direction along which the shift is carried out at step S68 may be any of the vertical, horizontal and oblique directions on the 3D referential image PIref. As shown in FIG. 23, the shift can be made along the first vertical direction i, and the line is transferred in the horizontal direction j to repeat the shift in the second vertical direction i. This shifting manner is repeated regularly (refer to a reference numeral SC in the figure). Oppositely to this, the shift can be made along the horizontal direction j, and the line is transferred in the vertical direction i to repeat the shift in the horizontal direction. Moreover, the shift may be performed obliquely.

Meanwhile, when the foregoing specifying steps have completed for all the plural determination points P, the determination at step S67 reveals YES during the repeated processing. This means that, every determination point P, an optimally focused sectional position has been detected in the depth direction passing through the position P on the 3D referential tomographic plane SS (including determination whether or not there is an optimally focused position). In this case, the processing proceeds to a connection process of the optically focused sectional positions.

Figure 24:
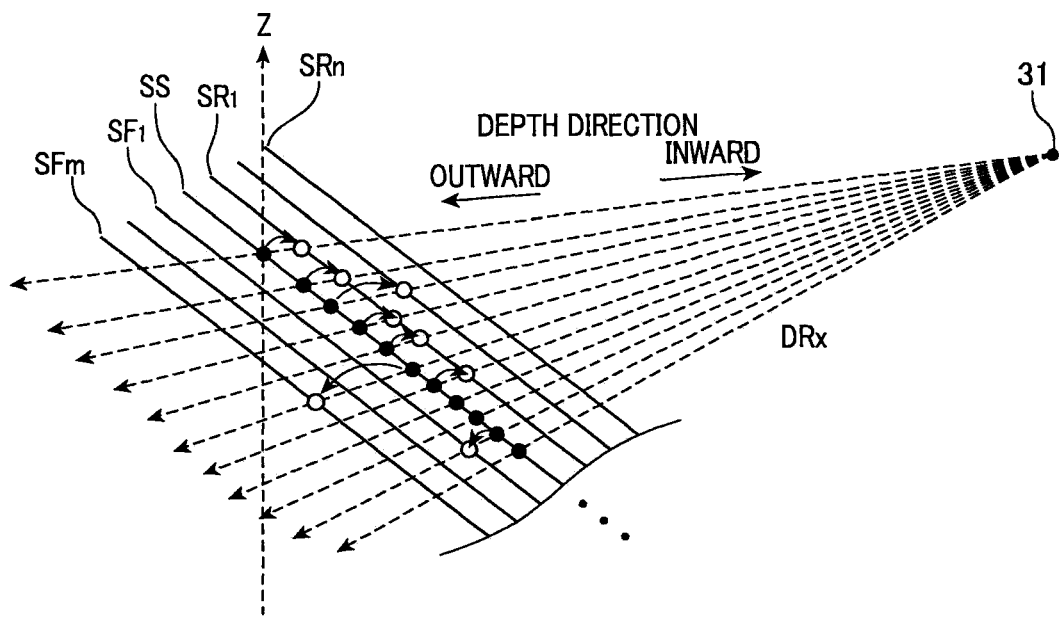
FIG. 24 is a perspective view explaining identification of the position of an optimally focused tomographic plane being identified every processing point and its abnormal identification.

When it is determined YES at the foregoing step S67, the image processor 56 reads data indicative of the optimally focused sectional positions specified and stored at step S65 (step S68). The data of these sectional positions show positions in each of the X-ray radiation directions DRx passing through each of the determination points P(x, y, z). This is pictorially exemplified in FIG. 24. In this drawing, filled circles indicate determination points P(x, y, z) on the 3D referential image PIref (i.e., the 3D referential tomographic plane SS). In this case, the vertical and horizontal directions of the curved 3D referential image PIref are denoted by (i, j). In FIG. 24, as shown by open circles, for example, an optimally focused sectional position at a determination point P(x00, y00, z00) for i, j=0, 0 is read as a position actually preset at the position of a tomographic plane SR1, which is shifted inwardly by one section (toward the X-ray tube side). An optimally focused sectional position at a determination point P(x01 y01, z01) for i, j=0, 1, which is next to the determination point for i, j=0, 0, is read as a position also actually present at the position of the tomographic plane SR2, which is shifted inwardly by one plane. Furthermore, an optimally focused sectional position at a determination point P(x02 y02, z02) for i, j=0, 2, which is next to the determination point for i, j=0, 1, is read as a position actually present at the position of a tomographic plane SR3, which is shifted inwardly by one plane further. In FIG. 24, for the sake of an easier understanding the process at step S68, only one position in the Z-axis direction (i.e., the vertical direction) are shown, but, at each of the positions in the Z-axis direction, the process at step S68 is performed.

The image processor 56 then performs removal of noise (step S70). In the example shown in FIG. 24, an optimally focused sectional position at a determination point P(x03 y03, z03) for i, j=0, 3 is read as a position actually present at the position of a tomographic plane SFm, which is shifted outwardly by no less than m-piece sections (toward the detector side). In such a case, the image processor 56 applies, for example, a threshold checking to a difference between the sectional positions to find out noise, thus regarding it abnormal data. Hence, the data of mutually adjacent sections are for example smoothed to smoothly connect the sections and replaced with a new set of smoothed positional data. Alternatively, data used for the data replacement may be produced by selectively giving priority to sectional data closer to the outside of the detector. As another alternative, instead of such compensation using the data replacement, abnormal data may simply be removed from data being processed. It is also possible that the abnormal data to be removed include data abnormal in the Z-axis direction.

The image processor 56 then connects the positions with noise removed (that is, the positions showing the enamel) and three-dimensionally smoothes the connected positional data, whereby a surface image tracing the enamel is produced (step S71). The data of this surface image are stored in the image memory 54.

The image processor 56 then displays the produced surface image, as a 3D autofocus image PIfocus which is a three-dimensional panoramic image all portions of which are automatically optimally focused, on the monitor 60 at a desired view angle (step S72).

Figure 25:
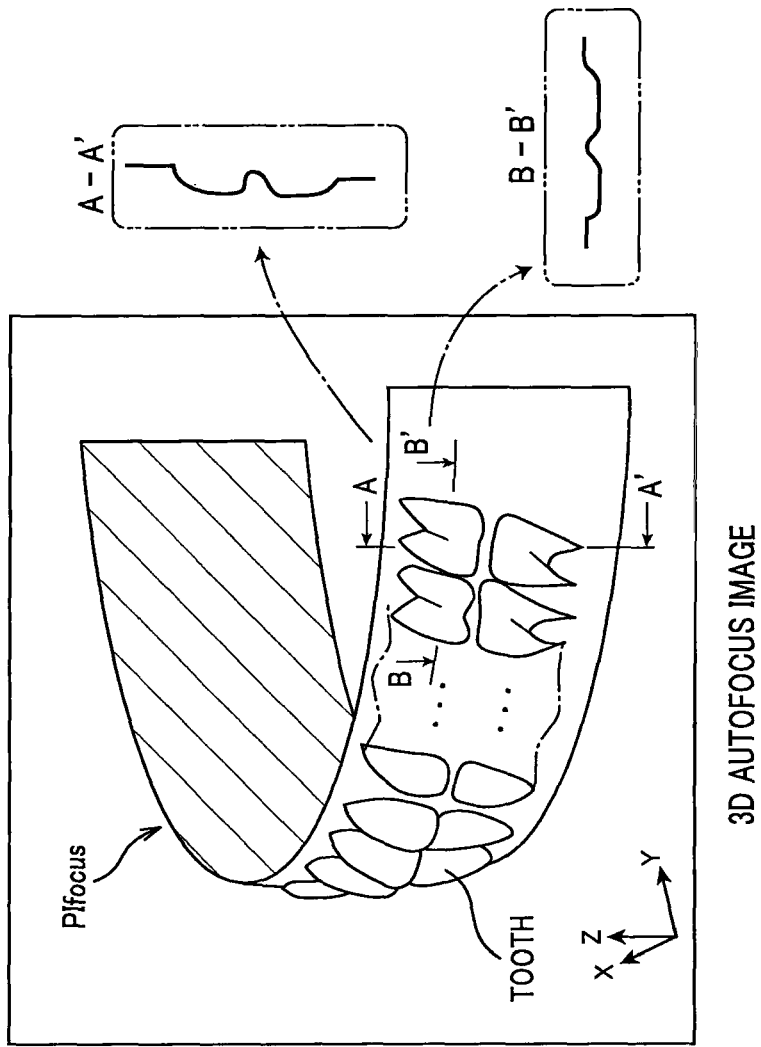
FIG. 25 is a view pictorially showing identification of the position of an optimally focused tomographic plane and a 3D autofocus image produced through smoothing.

Hence, as shown in FIG. 25, it is possible to provide the 3D autofocus image PIfocus at the desired view angle, where the 3D autofocus image structurally shows the tooth row of the oral cavity of the object P in the clearest manner. In the drawing, the curved horseshoe-shaped range S shows a range to display the 3D autofocus image PIfocus and solid lines show the real positions and shapes of the tooth row. As shown by an A-A' line and a B-B' line, portions such as part of the gum (alveolar bone), mandibular antra, the articulation of jaw, and the carotid artery can be depicted by a tomographic plane produced apart a given distance from the edges of the teeth (mainly the enamel) and the tomographic plane is projected three-dimensionally. In such a case, although it is not guaranteed that such portions other than the teeth are optimally focused, there will not be an unnatural feeling to the 3D panoramic images. Of course, the calculation for optimal focusing may be improved to optimally focus on such portions other than the teeth in the whole calculation, depending on purposes of diagnosis.

In this way, the produced 3D autofocus image PIfocus is entirely curved to trace the tooth row and its surface is rough. This "roughness" depicts the real position and shape (contour) of each of the teeth by densities of pixel values. The remaining parts can also be depicted with no unnatural feeling.

Hence, the autofocus image PIfocus indicating the real position and shape of the tooth row of each object P. The data to of this image are stored in the image memory 54.

(Production of the Second 3D Autofocus Image)

When the production of the foregoing 3D autofocus image (i.e., the first 3D autofocus image) has been completed, the image processor 56 produces the second 3D autofocus image. Practically the image processor 56 reads the image data of the second referential panoramic image PIst-2 into its work area from the image memory 54 (step S7), and, using the image data of the second referential panoramic image PIst-2, performs a subroutine which is according to steps S51-S72 in FIG. 10 (step S8). As a result, similarly to the foregoing, a 3D autofocus image is produced, which results from the imaging carried out at the second imaging time point T2.

(Estimation of Temporal Changes of Portion Being Imaged)

Figure 26:
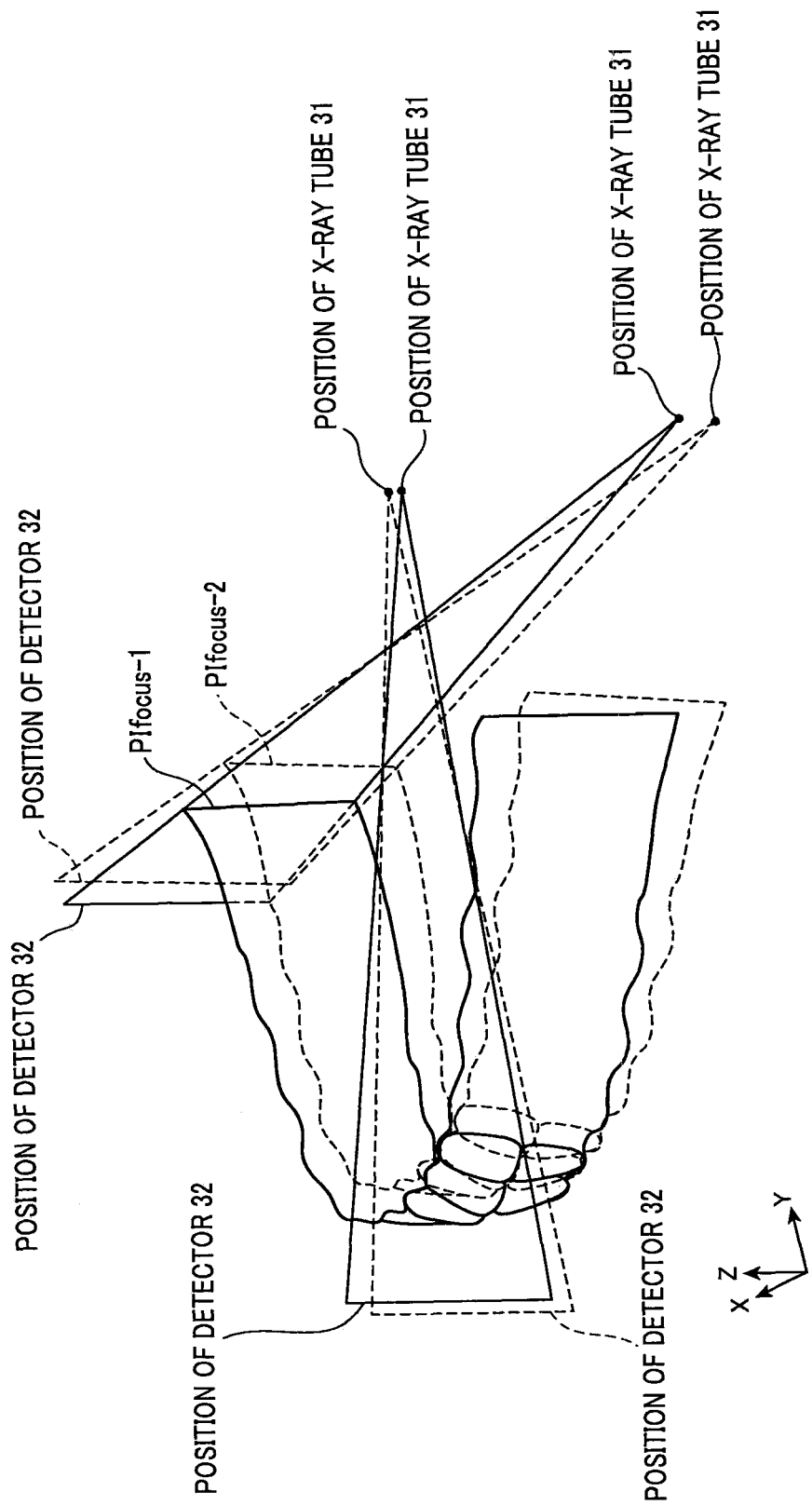
FIG. 26 is a view explaining a spatial positional relationship among two 3D autofocus images, the X-ray tube and the detector.

As stated above, the first and second 3D autofocus images PIfocus-1 and PIfocus-2 of the oral cavity of the same patient can be obtained as images scanned at different imaging time points T1 and T2. These images are shown in FIG. 26. In this figure, the shapes of the teeth are pictorially shown and the height of the image in its longitudinal direction is not shown.

As can be assumed from FIG. 26, it frequently occurs that the images of the oral cavity are positionally shifted from each other, because the imaging time points differ from each other, though there may be variations in the positional shift amount. This kind of shifts can happen even if the operator tried to position the patient's oral cavity precisely. In this case, it is difficult to capture an accurate temporal changes of the portion being imaged, i.e., from the two 3D autofocus images PIfocus-1 and PIfocus-2 spatially shifted from each other. Thus, when such temporal changes are desired to be detected, it is necessary to accurately align the spatial positions of the first and second 3D autofocus image PIfocus-1 and PIfocus-2 with each other.

(Spatial Alignment)

In order to perform the spatial alignment, to the position of the first 3D autofocus image PIfocus-1 produced at step S5, the position of the second 3D autofocus image PIfocus-2 produced at step S8 is aligned (step S9). Alternatively, this original image and the image being aligned to the original image may be opposite to each other in the alignment, so that the first 3D autofocus image PIfocus-1 is positionally aligned to the second 3D autofocus image PIfocus-2.

Figure 27:
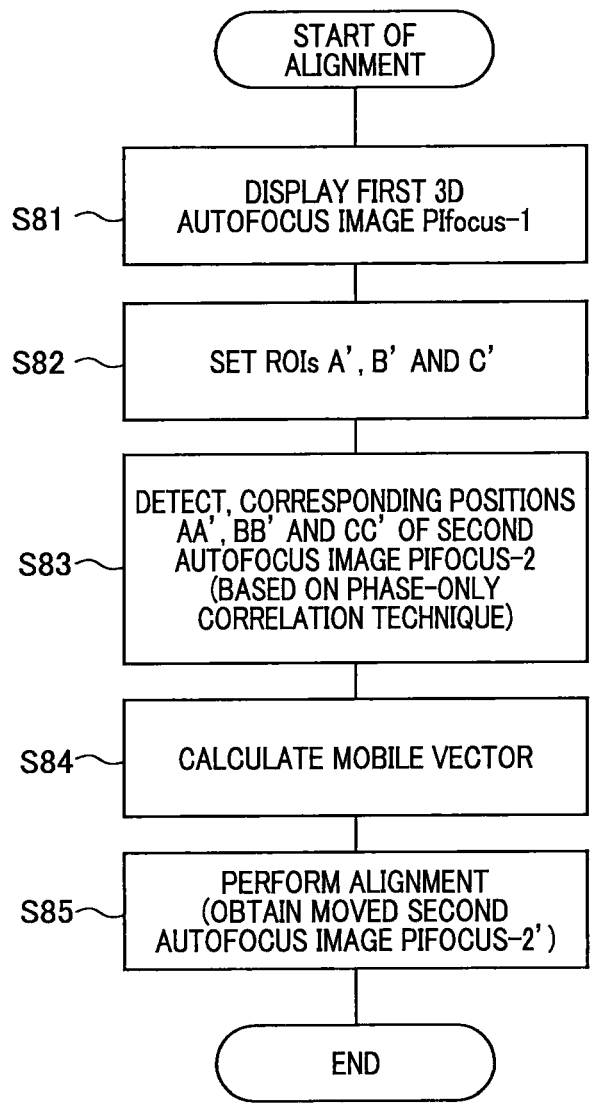
FIG. 27 is a flowchart outlining a process for aligning the two 3D autofocus images.

The process performed at step S9 is shown as a subroutine process in FIG. 27. The image processor 56 first displays the first 3D autofocus image PIfocus-1 on the monitor 60 (step S81).

Figure 28:
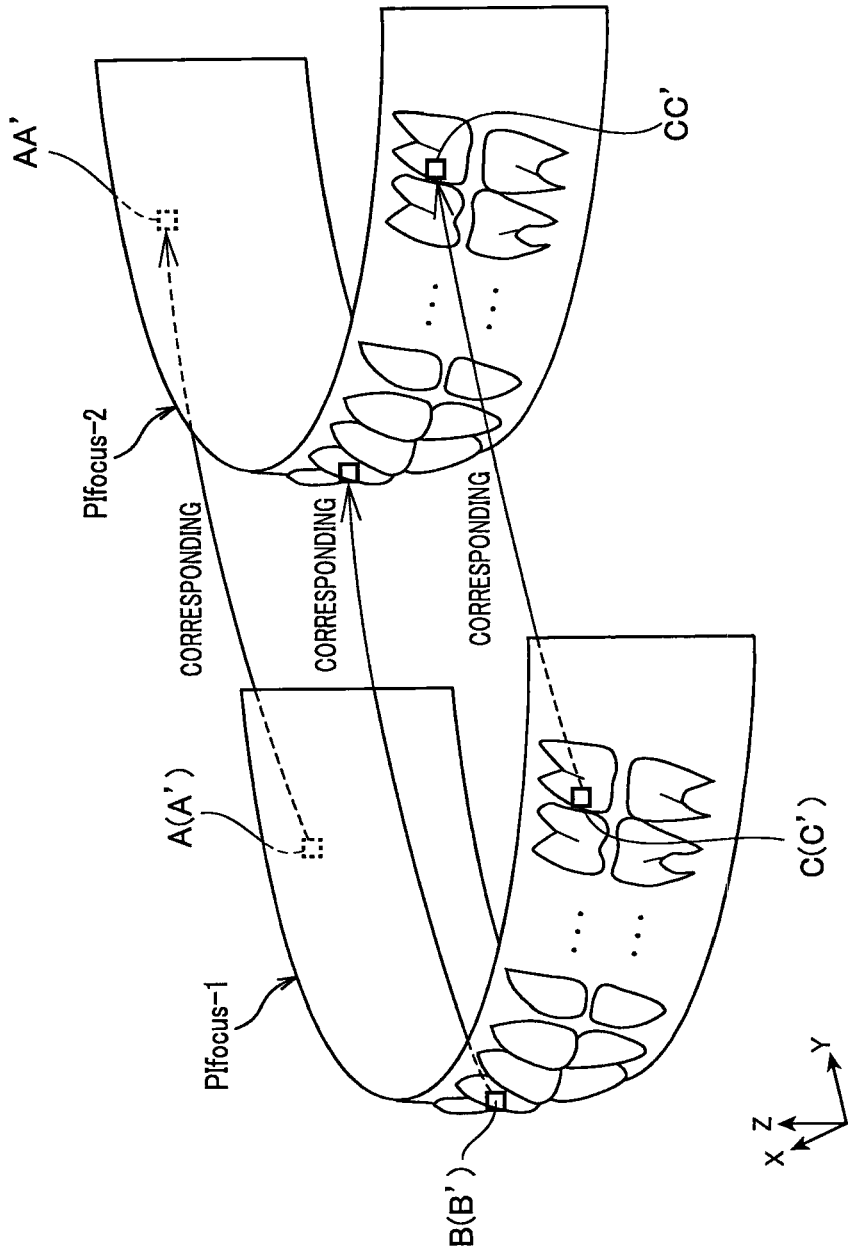
FIG. 28 is a view explaining a spatially correspondent relationship among ROI positions on the two 3D autofocus images.

The image processor 56 allows an operator to interactively set three small ROIs A', B' and C' on enamel portions of teeth in the first 3D autofocus image PIfocus-1 (step S82). This setting is shown in FIG. 28. Practically the ROIs A', B' and C' are set such that the operator specifies rectangular ROIs A, B and C of given sizes in enamel portions of teeth in the first referential panoramic image PIst-1 (refer to FIG. 8) and the positions of such ROIs A', B' and C' are projected to the first 3D autofocus image PIfocus-1 along the X-ray radiation directions DRx.

The number of ROIs is at least three. Four or more ROIs may be set, but at least three ROIs can uniquely define the spatial position of an object. In consideration of a lesser amount of calculation, it is preferable to use three ROIs. It is also preferable that distances between the three ROIs A', B' and C' are greater as much as possible. For example, two ROIs A' and C' are respectively set at centers of the enamel portions of any two teeth in the molar teeth on both sides, while the remaining ROI B' is set at the center of any one tooth in the anterior teeth. The reason why the ROIs are set on the enamel portions is that the frequency characteristic patterns PR1 and PR4, which have been described, are stable so that the positional accuracy for the optical focusing is higher than other portions. Three or more ROIs may be set on the upper and lower tooth rows. For example, two ROIs A' and C' are set on any two teeth in the molar teeth on both sides of the upper tooth row and one ROIB' is set on a tooth in the anterior teeth of the lower tooth row.

After this, the image processor 56 searches positions AA', BB' and CC' on the second 3D autofocus image PIfocus-2 respectively corresponding to the three ROIs A', B' and C' on the first 3D autofocus image PIfocus-1 (step S83; refer to FIG. 28). In the present embodiment, the positions AA', BB' and CC' on the second 3D autofocus image PIfocus-2 are specified as points which have the highest phase correlation to the three ROIs A', B' and C' on the first 3D autofocus image PIfocus-1. To decide such positions, the image processor 56 reads from the ROM 61 an algorithm for a phase-only correlation technique which is previously stored in the ROM, and perform processing according to this algorithm. This phase-only correlation technique is known for example by "A Palmprint Recognition Algorithm Using Phase-Only Correlation; Koichi ITO et al,; Meeting on Image Recognition & Understanding (MIRU 2006); Issued on July 2006".

Use of the phase-only correlation technique makes it possible to decide the corresponding positions AA', BB' and CC' on the second 3D autofocus image PIfocus-2. Then the image processor calculate mobile vectors from the three reference positions A', B' and C' to the searched positions AA', BB' and CC' respectively (the mobile vectors shows scaling, rotation, and parallel movement) (step S84).

Figure 29:
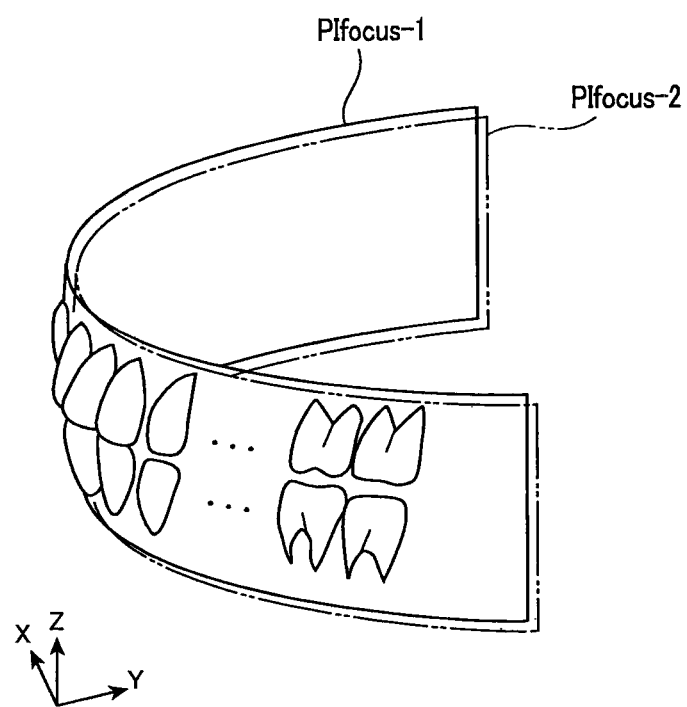
FIG. 29 is a view conceptually explaining the two 3D autofocus images aligned with each other.

Using such mobile vectors, processing for aligning the second 3D autofocus image PIfocus-2 to the first 3D autofocus image PIfocus-1 is performed (step S85). Practically the mobile vectors are used to move (with scaling, rotation, and parallel movement) the three positions AA', BB' and CC' to the three ROIs A', B' and C' on the first 3D autofocus image PIfocus-1, respectively. As a result, the second 3D autofocus image PIfocus-2' is moved as shown in FIG. 29, for example.

Alternatively, at step S85, the foregoing alignment can be performed several times in an asymptotic manner. Concretely the original image and a once-aligned image are aligned again with use of further three ROIs, and this alignment is repeated several times thereafter. This makes it possible to reduce errors accompanying with determining positions, which is inherent to the phase-only correlation.

(Depiction, Display Etc. of Temporal Changes)

Then the image processor 56 proceeds to step S10 shown step S10 in FIG. 5, where differences of pixel values between the first 3D autofocus image PIfocus-1 and the moved second 3D autofocus image PIfocus-2' are calculated pixel by pixel. This subtraction is performed by re-projecting the first 3D autofocus image PIfocus-1 and the moved second 3D autofocus image PIfocus-2' to the 3D reference plane SS along the X-ray radiation directions DRx directed to the respective pixel positions on the first 3D autofocus image PIfocus-1 (refer to a pictorial illustration in Fog 30). After this, each of the re-projected images is developed along the two-dimensional plane of the referential panoramic image PIst, and the subtraction is performed between those two-dimensional planes. By this subtraction, only image portions indicating temporal changes between the two 3D autofocus images PIfocus-1 and PIfocus-2' are depicted, thus producing a two-dimensional difference image.

The image processor 56 makes the monitor 60 display the 2D difference image PIdiff(2D) thereon (step S11). This example is pictorially shown in FIG. 31. As shown, only a partial image PA is depicted, which shows temporal changes between the two imaging time points T1 and T2. This 2D difference image PIdiff(2D) may contain some degree of distortion unavoidable during developing the three-dimensional planes to the two-dimensional plane, but this 2D image can provide the same interpretation feeling to interpreters who are familiar to the conventional panoramic images.

Figure 30:
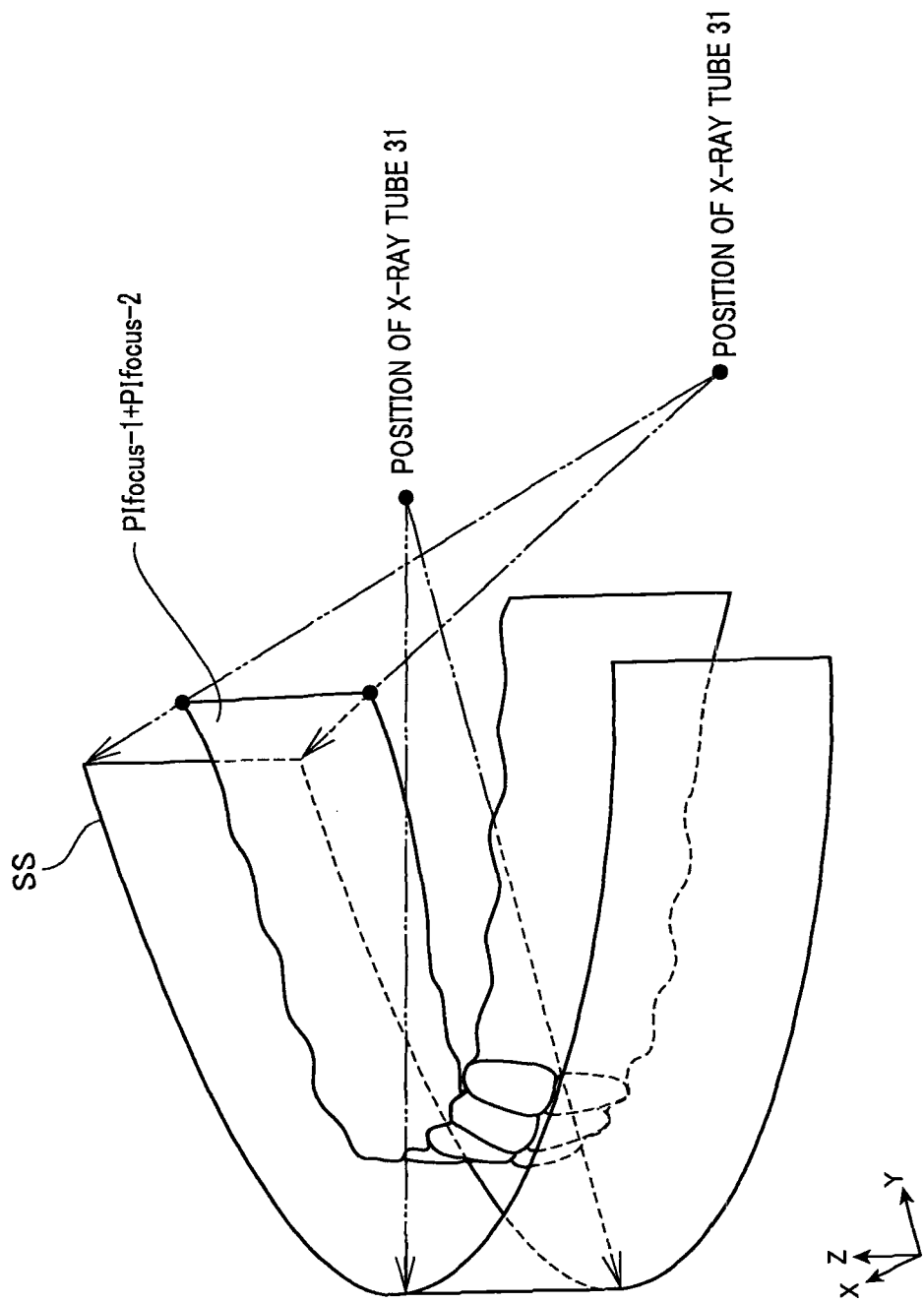
FIG. 30 is a view explaining a concept of processing for projecting the 3D autofocus image onto the 3D referential tomographic plane.
Figure 31:
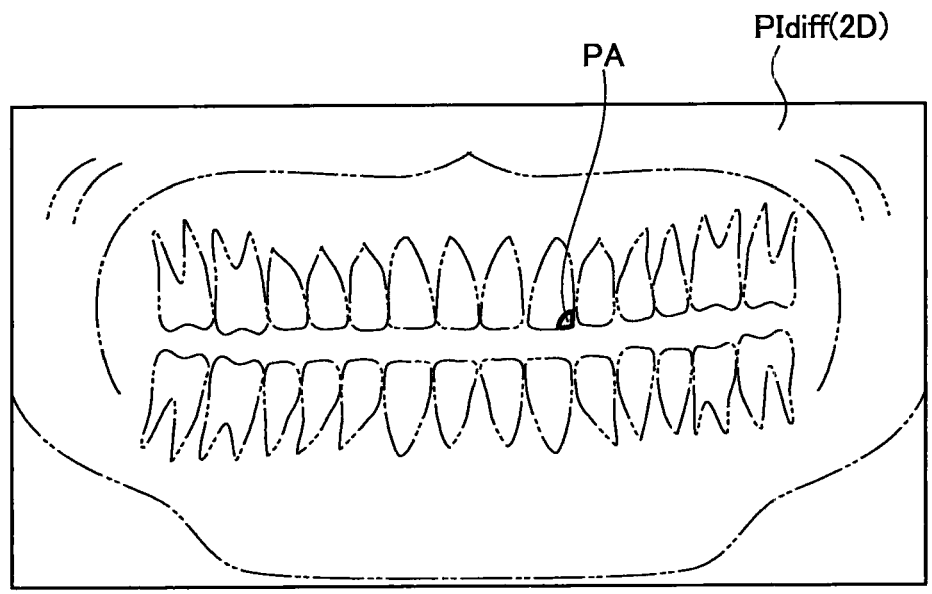
FIG. 31 is a monitor image displayed as a two-dimensional differential image, which is a result of difference between the two 3D autofocus images.
Figure 32:
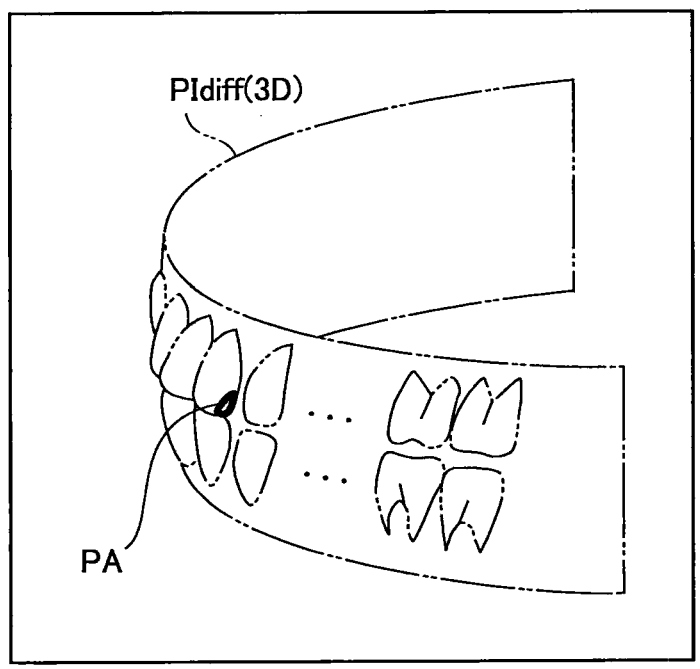
FIG. 32 is a monitor image displayed as a three-dimensional differential image, which is a result of difference between the two 3D autofocus images.

As an alternative technique, the foregoing subtraction can be performed on the 3D reference image SS. Practically, as shown in FIG. 30, each of the first 3D autofocus image PIfocus-1 and the moved second 3D autofocus image PIfocus-2' is re-projected onto the 3D reference plane SS along the X-ray radiation directions DRx, and the images re-projected on the 3D plane are then subjected to mutual subtraction pixel by pixel. In this case, there are depicted only partial images which show temporal changes between the two 3D autofocus images PIfocus-1 and PIfocus-2'. This can provide a 3D difference image PIdiff(3D). One such example is pictorially shown in FIG. 32, in which the 3D difference image PIdiff(3D) provides a temporal change as a partial image PA, which can be depicted stereoscopically.

Whichever of the 2D difference image PIdiff(2D) and the 3D difference image PIdiff(3D) is used, these images positionally correspond to the 3D autofocus images. Hence, distances such as longitudinal lengths of teeth can be detected by specifying a range on the 2D difference image PIdiff(2D) or the 3D difference image PIdiff(3D) and calculating the distance of a portion on the 3D autofocus images, which portion corresponds to the specified range. Hence the distance of the specified range can be provided.

Furthermore, the image processor 56 determines, interactively with an operator, whether or not the 2D difference image PIdiff(2D) (or the 3D difference image PIdiff(3D) should be colored for display (step S12). For the color display, a given color (for example, red) is applied to pixels whose difference values are more than zero (step S13), and the colored 2D difference image PIdiff(2D) is displayed (step S14). Thus, a remaining portion after the subtraction, that is, the portion PA where there has been occurred temporal changes are represented in colors alone, whereby a 3D panoramic image can be provided which allows an easier interpretation.

The image processor 56 further receives an operator's command and uses its command to determine whether or not a process for automatic recognition to decide if there is a lesion should be performed (step S15). In such automatic recognition, portions whose pixel values, that is, difference values, are equal to or higher than a predetermined threshold are recognized as being a lesion(s) (sep S16). Then this is followed by notification actions such as displaying a massage or flashing a display (step S17). In this way, a CAD (Computer Aided Design) function can be provided.

(Operations and Effects)

The panoramic imaging apparatus according to the present embodiment can provide operations and effects superior to the conventional, which are as follows.

First of all, differently from panoramic images produced by the conventional panoramic imaging apparatus, an image optimally focused on all the region of a tooth row is, at least, provided as a 3D autofocus image PIfocus (a 3D panoramic image). In this image, even if teeth are curved in the vertical direction, the real positions and shapes of the teeth are best focused point by point (i.e., every sampling point). In addition, the processing for the optimal focusing is automatically executed responsively to an operator's one-time command, resulting in representing a 3D autofocus image PIfocus. That is, an autofocus function can be obtained. Moreover, many variations for observing images are provided which include rotation and display of the 3D autofocus image PIfocus and display with a ROI enlarged locally. Hence, interpreters can easily examine an overall tooth row and the examination can be higher in its accuracy. It is therefore hardly necessary to re-perform the X-ray imaging, thus avoiding X-ray exposure from increasing. It is also preferred that the panoramic imaging apparatus of the present embodiment is used for a screening test.

In addition, changes of the enlargement factor, which depend on changes of the position of the rotation center during scanning (that is, changes of the rotation center RC of the pair of the X-ray tube 31 and the detector 32), are compensated during the processing for producing the 3D autofocus image PIfocus. Thus distortion resulting from changes of the enlargement factor is corrected, thereby providing images in which the real size and the real shape of an object are reflected more correctly.

In panoramic images produced by the conventional panoramic imaging apparatus, there occur changes of the enlargement factor in a tooth region from the molar teeth to the anterior teeth. Such changes become a factor that reduces the accuracy of measurement and understanding of distances and lengths in the produced image. In contrast, in the present embodiment, such an issue can be overcome, whereby it is possible to provide higher accuracy images and measurement data in which real sizes of objects are reflected without being distorted. Hence it is also preferred to use this apparatus in observing detailed structures of a tooth row which is an object being imaged.

In particular, even the 3D autofocus image PIfocus is re-projected to the 3D reference tomographic plane or the two-dimensional rectangular plane of the referential panoramic image as described, finally produced images may include some degree of distortion due to the re-projection. However, even in such a case, both the 3D autofocus image and the re-projected image positionally correspond to each other. Therefore, for example, distances such as the longitudinal of a tooth can be defined by specifying a desired range for distance measurement on the referential panoramic image. Depending on the range specified on the referential panoramic image, information of pixels in a range corresponding to the specified range on the 3D autofocus image is read. The distance of the specified range can be measured with precision.

Further, in the panoramic imaging apparatus according to the present embodiment, the three-dimensional positions of the X-ray tube 31 and the detector 32, which are positioned relative to the tooth row during data acquisition (scanning), are previously obtained. This means that, unlike the conventional, it is not necessary to previously measure information of distances of tomographic planes in the imaging space by using a phantom. Thus calibrating the apparatus can be made easier and calculation load of the image processor 56 can be alleviated.

Accordingly, all the region of a three-dimensional panoramic image is optimally focused in which a tooth row is three-dimensionally depicted so as to provide its actual state (position and shape) highly accurately in the image and distortion due to difference of the enlargement factor is removed effectively.

Meanwhile, according to the present embodiment, the two 3D autofocus images PIfocus-1, 2 of the oral cavity of the same patient imaged at different imaging points T1 and T2 are mutually aligned regarding to their positions, before being subtracted from each other. It is therefore possible to depict portions changing due to a lesion during a time interval between the two imaging points T1 and T2, thus providing a temporal evaluation.

Practically cavities and alveolar pyorrhea can be evaluated in terms of their temporal changes. Buried objects implanted in an implant treatment can also be traced regarding their temporal changes after being implanted. Further, a lesion at the roots of teeth can be detected with higher sensitivity. Diabrosis of bone supporting the tooth row can be understood in a more sensitive and qualitative manner. Meanwhile a cavity caused in an overlapped portion where lateral teeth are overlapped can be detected, which is difficult in the conventional panoramic image. Additionally information indicating that a lesion, such as a cavity, exists in which of teeth in the overlapped portion can be provided by information of tomographic plane positions which is used during the auto-focusing.

In this way, the subtraction performed after the precise alignment can provide doctors and examination technicians with very useful information for diagnosis. For instance, an interactive interpretation can be conducted between the apparatus and an interpreter. In cases any temporal changes cannot be read from the 3D difference image PIdiff displayed at step S11, the examination can be ended immediately. By contrast, if the 3D difference image PIdiff depicts portions from which lesions or injuries are suspected, the interpreter can proceed to finer interpretations. It can thus be said that the apparatus plays a greater role in not only treatments which should be done currently but also preventive medicine of teeth such as periodical health examination.

(Variations)

The foregoing embodiment has been described about a tooth row with the upper and lower jaws are depicted together, but it is just an example and not necessarily used in that way. For example, the upper and lower jaws may be separated from each other, in which the foregoing alignment is applied to each of the jaws. In order to perform such alignment, at steps S4 and S4' described, images of the upper and lower jaws are separated from each other using ROIs, and image data of the respective ROIs are stored in the memory. In addition, at steps S5 and S7, two 3D autofocus images of the separated upper jaw is read, and subjected to the autofocusing and processes thereafter. Though not shown, the processes from steps S5 to S10 are applied to two 3D autofocus images of the separated lower jaw. At step S11, those difference images are synthesized with each other for being displayed. It is also possible to set the ROI for only one of the tooth rows of the upper and lower jaws, so that only one of the upper and lower tooth rows can be subjected to the foregoing difference calculation. The image processor 56 may operate to interactively allow a user to select one or both of two operating methods; one is that the ROI is set on both the upper and lower jaws and the other is that the ROI is set on either one of the upper and lower jaws.

Figure 33:
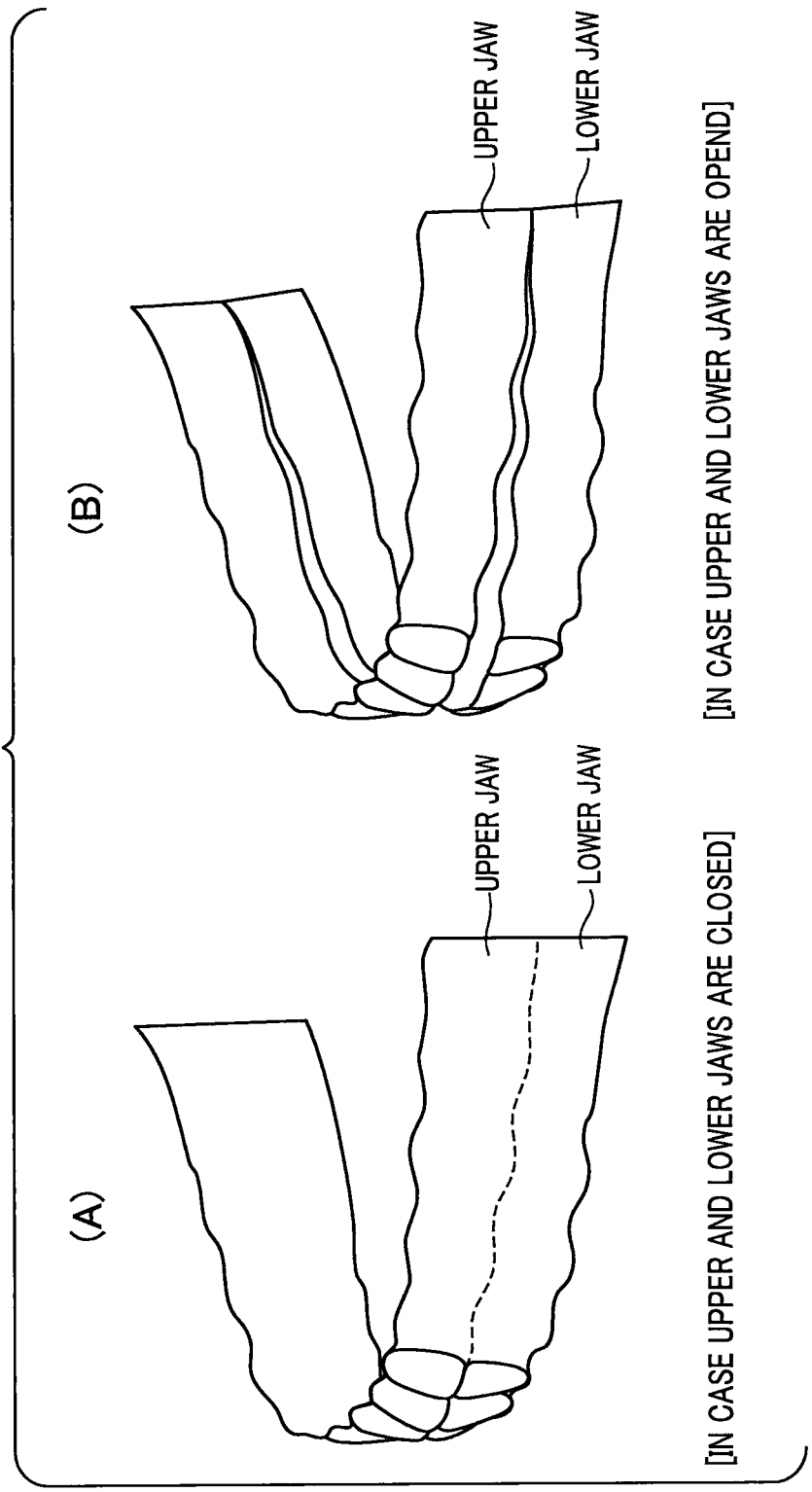
FIG. 33 is a view explaining jaw states where the upper and the lower jaws are closed and opened respectively when the upper and lower jaws are diagnosed separately from each other or together.

As a result, as shown in FIG. 33, in such an imaging case that the upper and lower tooth rows are contacted to each other at the initial imaging time points T1 (refer to (A) of FIG. 33) but such tooth rows are separated from each other at the second imaging time point T2 (refer to (B) of FIG. 33), both the upper and lower jaws can be selectively subjected to the 3D autofocusing. Hence, both 3D autofocus images can be aligned to each other in an accurate manner, whereby a difference image therebetween can to be calculated reliably. Of course, only one of the upper and lower jaws may also be used to calculate a difference image.

Figure 34:
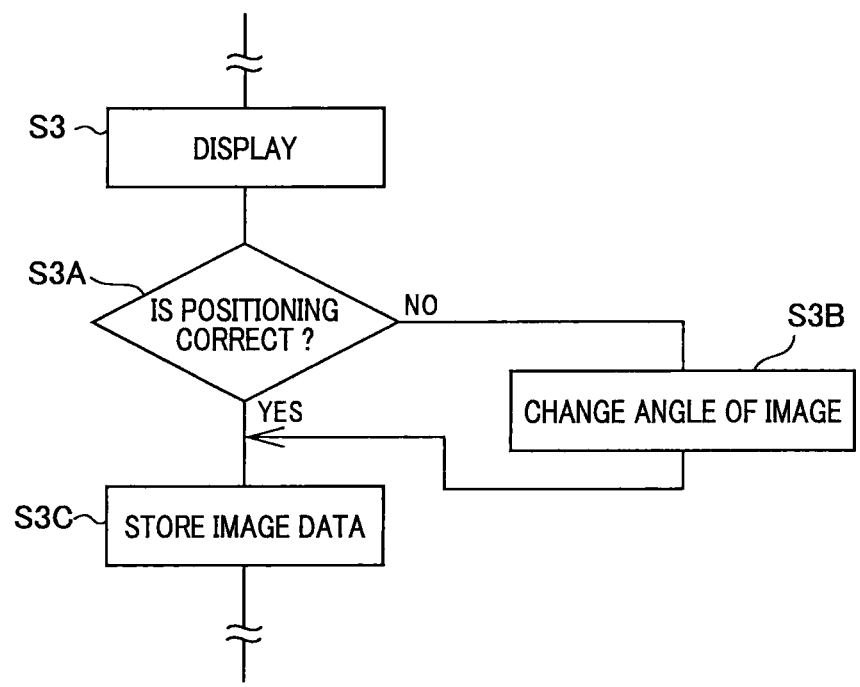
FIG. 34 is a partial flowchart explaining a process for changing an angle of the referential panoramic image to the angle of the jaw.
Figure 35:
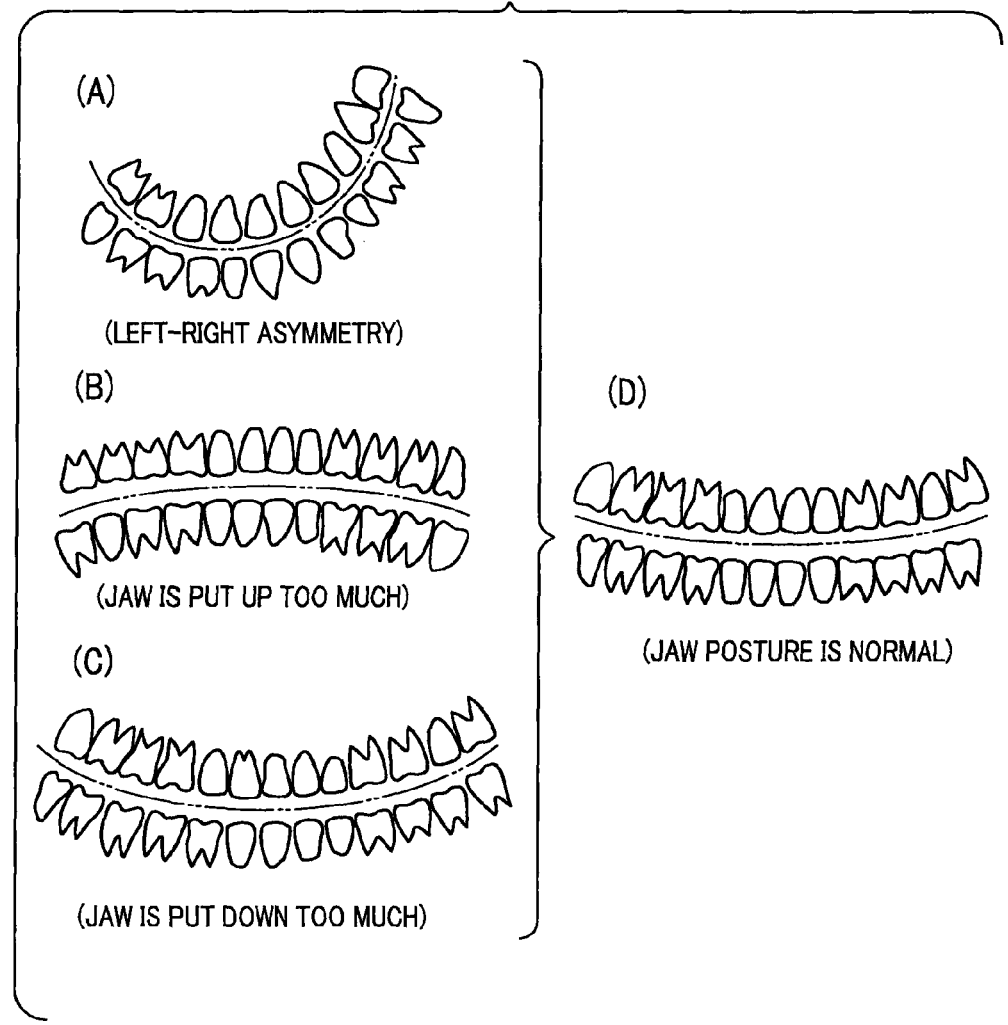
FIG. 35 is an image explaining changes of the angle of the referential panoramic image.

Alternatively, there can be provided another embodiment concerning storage of image data, which is performed at the foregoing steps S5 and S5'. In this case, an operator observes how the lateral center line is curved, which lateral center line divides the upper and lower tooth rows on the first and/or second referential panoramic images PIst-1 and PIst-2 displayed at steps S3 and S3'. Practically, through visual observation of such images, it is determined whether or not the initial positioning of a patient is correct (step S3A in FIG. 34). As a result of this visual observation, as shown in FIG. 35 (A)-(C), there are provided various cases including right and left asymmetry of a patient's jaw (refer to (A)), the jaw put up too much (refer to (B)), the jaw put down too much (refer to (C)). In such cases, the positional alignment performed at step S9 in FIG. 5 will not be easier. Hence, the angles of the referential panoramic images PIst-1 and PIst-2 are changed so that, as shown in FIG. 35(D), the jaw can be seen in a standard posture (step S3B). The data of the referential panoramic image with a curved center line observed after the proper angle adjustment are loaded into the image memory 54 (step S3C). In this way, it is easier to set the ROI when the 3D autofocus images are mutually aligned, improving the alignment in its accuracy, thus improving depiction of the difference information.

Alternatively, as a pre-process performed prior to the automatic alignment up to step S9 (except manual ROI setting), a selection step can be provided, in which an operator is given an option to select a combination of operator's manual rough alignment and then the alignment at step S9. This selection step is put between steps S8 and S9. When it is determined that the operator desire to manually align images up to some degree of alignment as a preparatory step, the image processor performs such preparatory alignment according to operator's commands. After this manual alignment, the processing proceeds to step S9. In this modification, it is enough for the image processor to mutually align two 3D autofocus images which are already spatially close to each other. When two original 3D autofocus images are distant from each other, the accuracy of the phase-only correlation technique can be maintained.

The foregoing embodiment has exemplified use of the two 3D autofocus images from which temporal changes are extracted. Instead, three or more 3D autofocus images which have been imaged at three different imaging time points may be used. In such a case, the first and second 3D autofocus images are used to extract temporal changes therefrom, and the second and third 3D autofocus images are used to extract temporal changes therefrom. Hence, information showing temporal changes tracing the imaging time to the second time point, and to the third time point.

In the foregoing embodiment and modifications, the alignment process for the two three-dimensional optimally focused images is performed using the algorithm based on the phase-only correlation. However this is just an example, and another algorithm may be employed which calculates minimums of absolute values or square sums of differences between pixels values of the images by using rotating and/or shifting the images.

Additionally, in the foregoing dental panoramic imaging apparatus, the pair of the X-ray and the detector may be installed on the ceiling. As an alternative, the apparatus can be mounted on an examination car or installed in a hose, if being compact in size and movable in structure.

The detector which can be employed in the radiation imaging apparatus of the present invention is not limited to the digital type of CdTe detector, but photon-counting type detectors can also be employed. Such photon-counting type detectors are known by for example Japanese Patent Publication JP-A-2004-325183.

The detector used by the radiation imaging apparatus according to the present invention is not always limited to use of the same type of detector. It is necessary to change an amount of energy of the X-ray depending on types of objects being imaged, so that material of the X-ray detecting elements may be selected in accordance with X-ray absorbing coefficients tuned to the necessary amount of X-ray energy. When it is necessary to generate larger amounts of energy, materials such as LaBr3, CdTe, CZT, and GOS can be adopted for the X-ray detecting elements. By contrast, for smaller amounts of X-ray energy, materials such as Si, CdTe, CZT, and CsI can be adopted for the X-ray detecting elements.

Further, the display mode is not limited to displaying the three-dimensional panoramic image (surface image). For example, from the profile in the tomographic plane positions versus the values of sums of squares of amplitude shown in FIG. 15, a width assumed to be focused can be obtained from the tomographic planes and the frequency characteristics, and using the width, the thicknesses of a tooth and/or the alveolar bone, that is, the thicknesses of those in the depth direction, to can be measured. When a configuration to obtain this measurement information can be applied, together with the foregoing photon-counting type detector, to the alveolar bone close to the first false molar, bone mineral content can be measured quantitatively.

When the imaging according to the present invention is applied to the mandibular antra or portions close thereto in the oral cavity, it is possible to provide, to some extent, image information about the stereoscopic structure of the mandibular antra. Moreover, comparing a bilateral difference in the image makes it possible to detect inflammation in the mandibular antra (empyema) in a more accurate manner more than the conventional. Similarly, when the imaging according to the present invention is applied to the carotid artery or portions close thereto, calcification of the carotid artery, which is assumed to be one of the reasons for arterial sclerosis, can be clearly displayed three-dimensionally, providing more accurate diagnostic information compared to the conventional.

The radiation imaging apparatus according to the invention will not be limited to applications for the dental panoramic imaging apparatus, but can be put into practice in applications where the tomosynthesis technique is used to understand the three-dimensional shapes (positions) inside an object. Such applications include mammography using the tomosynthesis technique and an X-ray scanner for lung cancer in the medical field. Further, the radiation imaging apparatus according to the invention can be applied to nuclear medicine diagnosis apparatuses called emission CT (ECT) apparatuses such as a gamma camera and a SPECT apparatus. In this application, gamma-rays radiated from RI (radioisotope) administered into an object are acquired by a detector via a collimator with holes opened in a designated direction. In this case, the RI and the collimator compose the radiation emitting source.

In addition, the number of detectors mounted in the radiation imaging apparatus of the present invention is not always limited to one, but may be two or more. Such two or more detectors can be driven as one unit or in parallel in a modality.

The radiation imaging apparatus of the present invention can also be applied to industrial applications, which include acquiring information about contents of products or commodities carried by a belt conveyor and positions of such products or commodities, inspecting three-dimensional structures of a flexible substrate connected to a flat panel display, acquiring information about three-dimensional distributions and sizes of holes in a mold, and acquiring positional information of contents in baggage screening in the airport. Objects being imaged can be moved linearly, in a circle, in a curve or in other ways. That is, the 3D referential tomographic plane can be set as a tomographic plane or section which is flat, cylindrical, or curved.

In particular, in the foregoing industrial applications, an object being imaged is allowed to move relatively to the pair of the X-ray tube and the detector, if necessary. Further, some reasons in the mechanical design permit only the detector to be moved relatively to an object being imaged or a patient and the radiation source.

INDUSTRIAL APPLICABILITY

According to the present invention, it is possible to provide a three-dimensionally focused image, in which image distortion due to differences in the enlargement factor is almost removed and the real position and shape of a region being imaged of an object is depicted at a higher precision. Hence such three-dimensionally focused images can be used to provide spatial information indicative of temporal changes of the same region being imaged of the same object, thus providing higher industrial availability.

DESCRIPTION OF REFERENCE NUMBERS

1 Dental panoramic imaging apparatus (radiation imaging apparatus)
12 Computer
14 Imaging unit
31 X-ray tube (radiation tube)
32 Detector
33 Collimator
41 High-voltage generator
53 Buffer memory
54 Image memory
55 Frame memory
56 Image processor
57 Controller
58 Operation device
60 Monitor

What is claimed is:
1. A radiation imaging apparatus, comprising:
a radiation emitting source including an X-ray tube radiating an X-rays;
a radiation detector detecting the X-rays and outputting, every frame, electric digital two-dimensional data corresponding to incidence of the X-rays to the radiation detector, the X-ray tube and the radiation detector being positioned to be opposed to each other with an object located therebetween;
moving means for moving a pair of the X-ray tube and the radiation detector such that the X-rays are scanned to focus on a three-dimensional (3D) referential tomographic plane of the object, the referential tomographic plane being curved in a real space;
data acquiring means for acquiring, every frame, the data outputted from the radiation detector while the pair of the X-ray tube and the radiation detector is moved relative to the object by the moving means;
image producing means for producing two three-dimensional optimally focused images on the basis of the data acquired by the data acquiring means at different two time points from the same portion to be imaged of the object, the portion to be imaged of the object being optimally focused and reflecting an actual position and shape of the portion therein and being an oral cavity containing a tooth row of the object;

aligning means for mutually aligning spatial positions of the two three-dimensional optimally focused images produced by the image producing means at the different two time point; and difference calculating means for calculating differences, pixel by pixel, between the two three-dimensional optimally focused images mutually aligned by the aligning means, wherein the image producing means comprises:

referential-plane image reconstructing means for reconstructing, as a referential-plane image, a panoramic image of the tooth row based on the data acquired by the data acquiring means, the panoramic image being produced by projecting the referential tomographic plane onto a detection surface of the detector, tomographic plane setting means for setting a plurality of tomographic planes along the 3D referential tomographic plane in a direction opposed to the 3D referential tomographic plane, pixel value calculating means for calculating pixel values of each of the plurality of tomographic planes, position identifying mean for identifying optimally focused sampling points of the portion being imaged based on image data of both the 3D referential tomographic plane and the plurality of tomographic planes to which the pixel value calculating means provides the pixel values, pixel value providing means for providing the sampling points identified by the position identifying means, with pixel values based on the pixel values at the sampling points corresponding to the panoramic image and being present in a viewing direction from the X-ray tube to the detector via the respective sampling points, tooth row detecting means for detecting the tooth row by recognizing the 3D referential tomographic plane provided at the sampling points to which the pixel values are provided by the pixel value providing means and a characteristic pattern shown by pixel values of the plurality of tomographic planes, classification means for classifying substances every characteristic shown by the same type of substance based on the frequency characteristic at the respective sampling points, and smoothing means for smoothly connecting the substances, classified by the classification means, such that noise is removed from the sampling points of the tooth row decided by the tooth row deciding means.

2. The radiation imaging apparatus of claim 1, wherein the aligning means comprises marking means for marking a plurality of specific positions on either one of the two three-dimensional optimally focused images, and fitting means for fitting a remaining one of the two three-dimensional optimally focused images to the one of the two three-dimensional optimally focused images on the basis of the specific positions marked on the one of the two three-dimensional optimally focused images by using a specific algorithm.

3. The radiation imaging apparatus of claim 2, wherein the algorithm is an algorithm based on a phase-only correlation method.

4. The radiation imaging apparatus of claim 1, wherein the apparatus comprises position deciding means for deciding, through calculation, which of the pixels showing the difference results calculated by the difference calculating means belong to which of the 3D reference tomographic plane and the plurality of tomographic planes.

5. The radiation imaging apparatus of claim 1 further comprising:

lesion determining means for automatically determining whether or not a region showing the difference results calculated by the difference calculating means is a lesion in the portion to be imaged, and notification means for notifying an operator of a fact the lesion determining means has determined that the region is a lesion.

* * * * *